(12) United States Patent
Lukasiewicz et al.

(10) Patent No.: US 9,382,338 B2
(45) Date of Patent: Jul. 5, 2016

(54) POLYSACCHARIDE AND DERIVATIVES THEREOF, SHOWING AFFINITY TO FICOLIN-3, METHOD OF PREPARATION AND USE

(75) Inventors: Jolanta Lukasiewicz, Wroclaw (PL); Anna Swierzko, Lodz (PL); Maciej Cedzynski, Lodz (PL); Czeslaw Lugowski, Wroclaw (PL); Anna Maciejewska, Swiebodzice (PL); Wojciech Jachymek, Wroclaw (PL); Tomasz Niedziela, Wroclaw (PL)

(73) Assignees: INSTYTUT BIOLOGII MEDYCZNEJ POLSKIEJ AKADEMII NAUK, Lodz (PL); INSTYTUT IMMUNOLOGII I TERAPII DOSWIADCZALNEJ PAN, Wroclaw (PL)

( * ) Notice: Subject to any disclaimer, the term of this patent is extended or adjusted under 35 U.S.C. 154(b) by 95 days.

(21) Appl. No.: 13/703,278

(22) PCT Filed: Jun. 11, 2011

(86) PCT No.: PCT/PL2011/050024
§ 371 (c)(1),
(2), (4) Date: Feb. 28, 2013

(87) PCT Pub. No.: WO2011/155859
PCT Pub. Date: Dec. 15, 2011

(65) Prior Publication Data
US 2013/0266971 A1    Oct. 10, 2013

(30) Foreign Application Priority Data
Jun. 11, 2010    (PL) .......................................... 391475

(51) Int. Cl.
*C08B 37/00*    (2006.01)

(52) U.S. Cl.
CPC ............ *C08B 37/00* (2013.01); *C08B 37/0003* (2013.01); *C08B 37/006* (2013.01); *G01N 2333/4724* (2013.01)

(58) Field of Classification Search
None
See application file for complete search history.

(56) References Cited

PUBLICATIONS

Tsujimura et al. 2001 (Detection of serum thermolabile b-2 macroglycoprotein (Hakata antigen) by enzyme-linked immunosorbent assay using polysaccharide produced by *Aerococcus viridans*; Clinical and Diagnostic Laboratory Immunology 8(2):454-459).*
Lukasiewicz et al. 2009 (Two Kdo-Heptose Regions Identified in Hafnia alvei 32 Lipopolysaccharide: The Complete Core Structure and Serological Screening of Different Hafnia O Serotypes; J Bacteriology, 191(2):533-544.*
Goldblatt 2000 (Conjugate Vaccines; Clin Exp. Immunol; 119:1-3).*
Caroff et al. 2003; Structure of bacterial lipopolysaccharides, Carbohydrate Research, 338:2431-2447.*
Ravenscroft et al. 1995; 3-Deoxy-octulosonic-acid-containing hexasaccharide fragment of unusual core type isolated from Hafnia alvei 2 lipopolysaccharide; Eur. J. Biochem. 227: 889-896.*
Estrid Hein et al., Molecular Immunology, vol. 46, p. 2843 (2009).
Ewa Katzenellenbogen, FEMS Immunology and Medical Microbiology, vol. 45, pp. 269-278 (2005).
Mitsushi Tsujimura, et al., Clinical and Diagnostic Laboratory Immunology, vol. 8, No. 2, pp. 454-459 (2001).
Mitsushi Isujimura, et al., Clinica Chimica Acta, vol. 325, pp. 139-146 (2002).

* cited by examiner

*Primary Examiner* — Gary Nickol
*Assistant Examiner* — Mary Lyons
(74) *Attorney, Agent, or Firm* — Law Office of Salvatore Arrigo and Scott Lee, LLP

(57) ABSTRACT

The invention relates to bacterial lipopolysaccharide and its components, especially native and chemically modified polysaccharides isolated from *Hafnia alvei* lipopolysaccharides, as well as conjugates of these polysaccharides with carriers and methods for their preparation and methods to use of these substances as ligands for human ficolin-3.

4 Claims, 10 Drawing Sheets

Figure 1A:
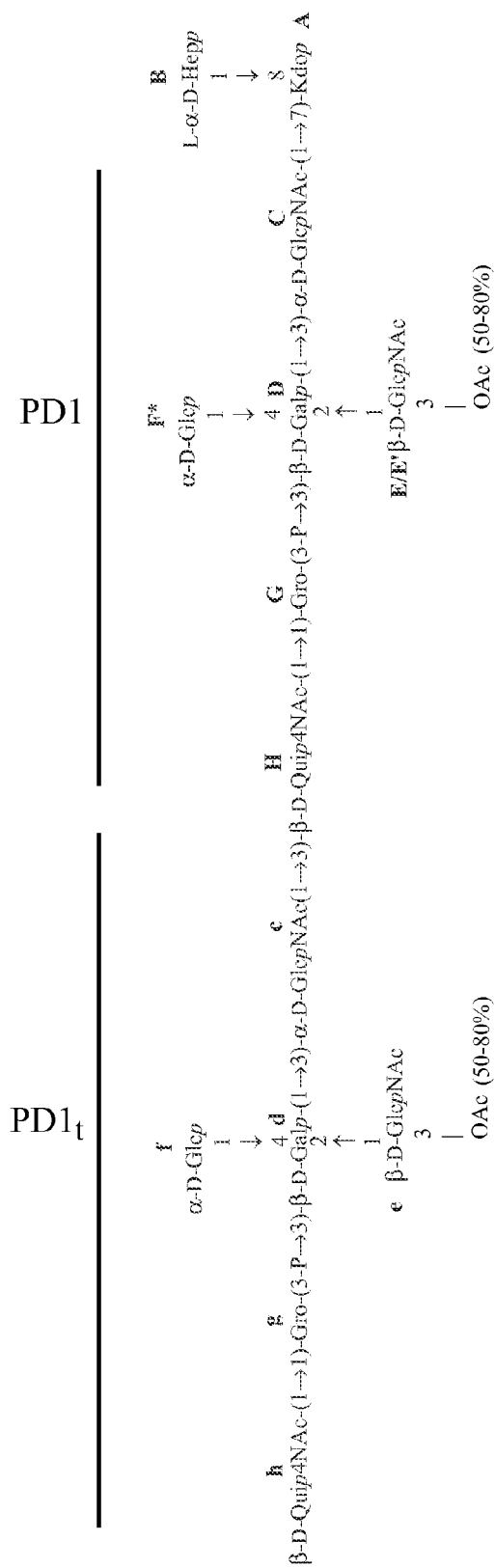

POLYSACCHARIDE AND DERIVATIVES THEREOF, SHOWING AFFINITY TO FICOLIN-3, METHOD OF PREPARATION AND USE

This application is the U.S. national stage of International Application No. PCT/PL2011/050024, filed Jun. 11, 2011, which claims the benefit of Polish Application No. PL391475, filed Jun. 11, 2010, both of which are hereby incorporated herein by reference.

The invention concerns a bacterial lipopolysaccharide and its parts, especially native and chemically modified polysaccharides isolated from the lipopolysaccharides of *Hafnia alvei*, conjugates of these lipopolysaccharides with carriers, and application of the polysaccharides alone, as well as their conjugates, as ligands for human ficolin-3 (ficolin-H, Hakata antigen) in the measurement tests. The polysaccharides isolated from lipopolysaccharides of *H. alvei* and conjugates thereof with carriers can also be used as ligands for the recombinant forms of human ficolin-3, the homologs and analogues of human ficolin-3 present in other species, the recombinant forms of homologs and analogues of human ficolin-3 present in other species.

Lipopolysaccharides (LPS, endotoxin), composed of the polysaccharide and lipid parts, are amphiphilic molecules located at the surface of Gram-negative bacterial cells (Rietschel et al., 1996). Lipopolysaccharides constitute an integral outer membrane component of the bacterial cell envelope, that are unique and required for function and survival of Gram-negative bacteria. Lipopolysaccharides play an important role as virulence factors of Gram-negative bacteria in cases of sepsis and septic shock (Hoist et al., 1996). Due to the biological activities LPS is also named endotoxin.

Regardless of the lipopolysaccharide origin, the molecule isolated from smooth forms of bacteria, is distinguished by the following general building blocks, comprising three regions: (1) O-specific chain (O-specific polysaccharide)—a polymer composed of repeating oligosaccharide units, showing high structural variability and defining the sero-specificity of LPS(O-antigenic specificity); (2) core oligosaccharide—a region with the limited structural variability within species, that can be sub-divided into the segments: distal—termed the outer core, hexose region and proximal—termed the inner core, heptose region in relation to the lipid A (3) lipid A—a region that anchors the LPS in the outer membrane of the Gram-negative bacteria cell envelope and in most of Enterobacteriaceae built of $\beta$-D-GlcpN-(1→6)-$\alpha$-D-GlcpN disaccharide substituted by fatty acids, phosphate groups and saccharide or non-saccharide substituents (Rietschel, Brade et al., 1996). Lipid A is substituted by the core oligosaccharide through the ketosidic linkage between the Kdo molecule of the core oligosaccharide and the $\beta$-D-GlcN residue at the non-reducing end of the carbohydrate backbone of the lipid A. The biological activities attributed to the lipopolysaccharide are strictly related to the structural features of this region, which constitutes the toxicity centre of the lipopolysaccharide.

Similarly to bacterial DNA, viral RNA, mycobacterial glycolipids, teichoic acids, yeast mannans and lipoproteins of Gram-positive bacteria, lipopolysaccharides constitute the so called pathogen-associated molecular pattern, PAMP. These molecules are the characteristic structures present on pathogens—they are not present in higher organisms, but for microorganisms they are important to such an extent, that they are not subjected to frequent changes in the evolution process (Aderem i Ulevitch, 2000). Therefore the cells of immune system have developed a universal system of receptors, that are able to recognize such structures and induce a fast defensive reaction (the receptors include: Toll-like receptors, scavenger receptors, mannose receptor, as well as a verity of soluble molecules, recognizing molecular patterns (PAMP), comprising components of the complement system, collectins and anti-bacterial peptides.

The main region responsible for biological activity of lipopolysaccharides is lipid A, a region of the lowest structural variability. The CD14/TLR4/MD-2 receptor complex, present on the surface of macrophages, monocytes, neutrophils and B-lymphocytes, is the main receptor, involved in the mechanisms of innate immunity and binding of the lipid A region (Aderem i Ulevitch, 2000). Activation of the signalling pathway is followed by the production of pro-inflammatory mediators by target cells for LPS.

Other regions of the LPS, the O-specific polysaccharide and the core oligosaccharide, are the segments that modulate lipid A activity, following the LPS-CD14/TLR4/MD-2 interaction. Because of its characteristic-high structural variability, the O-specific polysaccharide and the core oligosaccharide activate the mechanisms of innate immunity to a lesser extent. However, in the group of all LPS structures analysed to date, molecules capable of activation of the innate immunity factors, other than described above, were identified. The structures of certain O-specific chains and core oligosaccharides can be recognized by such components as, for example: mannan-binding lectin (MBL) and other human lectin-like proteins. Lectins bind to specific carbohydrate structures on the surface of the pathogen, and then they activate adequate effector mechanisms, such as: activation or inhibition of the complement system, agglutination, opsonisation (facilitating endocytosis), inhibition of microorganism growth and modulation of proinflammatory or allergic response. The selectivity and the ability to distinguish between the foreign and the host structures by lectins are based on spatial differences between the recognized carbohydrates (Thiel, 2007).

Besides MBL, the activation of the complement, one of the mechanisms of innate immunity relates to the recently discovered group of lectins, named ficolins, which have been only poorly characterized for its ligands. In humans the group comprises ficolin-1 (M), ficolin-2 (L) and ficolin-3 (H), and in mice: ficolins A and B (Thiel, 2007).

The complement system is a group of several dozen mutually dependent proteins present in blood and other bodily fluids. Complement activity is based on the activation of enzyme cascade, leading to a series of reactions that play an important role in the onset of immune response and proinflammatory reactions. Three ways of complement activation have been identified: the classical pathway, the lectin pathway and the alternative pathway. They differ primarily in their initiation stages. The activation of each pathway takes place as a cascade of events, ultimately leading to: (i) opsonisation of microorganisms-(facilitates phagocytosis), (ii) chemotaxis of scavenger cells to the site of inflammation, (iii) elimination of modified or damaged host cells, (iv) direct lysis of bacterial cells, viruses, parasites and fungi, and (v) initiation of a inflammatory reaction.

For the activation of the complement cascade through the lectin pathway, MBL, ficolin-1 (M), ficolin-2 (L), ficolin-3 (H) are the key molecules recognizing the Pathogen-Associated Molecular Pattern (PAMP). All of these proteins have a similar structural scheme. They have an oligomeric structure composed of the basic subunit of three polypeptide chains. Each chain is built of the N-domain, containing a large number of cysteine residues, the collagen-like region and the ligand recognizing domain. For MBL protein it is a typical lectin domain CRD (a carbohydrate-recognition domain).

For ficolin it is a fibrinogen-like region (FBG), having a different structure (Thiel, 2007).

Among the listed lectins, the current state of the art best describes MBL protein and the ligands derived from pathogens bound by this protein. It is known that MBL shows specificity for the following monosaccharides: D-mannose, L-fucose, N-acetyl-D-glucosamine, D-glucose, occurring commonly as components of surface structures in pathogens such as Gram-negative and Gram-positive bacteria, yeast, parasites, mycobacteria and viruses (Degn et al., 2009).

Unlike molecular mechanisms of activation of the MBL-dependent lectin pathway, activation of the complement through the lectin pathway by ficolins and in particular its initial stages, i.e. the interaction of the ficolins with PAMP, are the least characterized mechanism within the complement system. In terms of serum concentrations, ficolins constitute a dominant fraction of molecules responsible for the activation through the lectin pathway. In the serum the average concentration of ficolin-3 (H), ficolin-2 (M) and ficolin-1 (L) is 25 µg/ml, 5 µg/ml and 0.1 µg/ml, respectively, and the MBL level value is approximately 1-3 µg/ml (Garred et al., 2009). The specificity of ficolins to ligands is poorly known. Knowledge of this topic is limited to the observation that the potential ligands for ficolins can be N-acetyl groups of naturally occurring sugars such as GlcNAc, GalNAc as well as N-acetylated glycine. The ligands for ficolins also include artificially derived ligands such as, N-acetylated bovine serum albumin (BSA-NAc), BSA-GlcNAc, and N-acetylated low-density lipoproteins (LDL-NAc). It has been demonstrated that ficolins are also able to bind C-reactive protein (CRP) (Thiel, 2007). All ficolins, as well as the MBL bind the MASP serine proteases (MBL-associated serine proteases), and this allows them to initiate an activation of the complement through the lectin pathway. The MASP-2 enzyme plays a key role in this process. Among the molecular patterns associated with pathogens recognized by human ficolins only a few examples, that are fairly diverse with respect to chemical structures, have been reported in the literature. Much is known about ligands for ficolin M and L. Among ligands for ficolin-1 (M) lipoteichoic acid of Gram-positive bacteria, bacterial surface antigens of *Staphylococcus aureus* and *Salmonella typhimurium*, 1,3-β-D-glucan of fungi, sialic acids and their derivatives O-acetylated at position 9 (Le Goût et al., 2009) were identified. This lectin shows an affinity for N-acetyl-D-glucosamine (GlcNAc), N-acetyl-D-galactosamine (GalNAc) and sialic acid (Neu5Ac), binding them through acetyl groups (Garlatti et al.; Liu et al., 2005; Matsushita, 2007; Runza et al., 2008).

This feature, which is typical for the ficolins, facilitates binding to a non-saccharide ligands such as N-acetyl-L-cysteine and acetylated albumin (Wittenborn et al., 2010). The binding site, located in the fibrinogen domain, is homological to the S1 site of tachylectin. Ficolin M recognizes the surface structures of certain strains of streptococci, staphylococci, *E. coli* and *S. enterica* (Runza, Schwaeble et al., 2008). The ficolin-2 (L) shows an affinity for N-acetyl-D-glucosamine, N-acetyl-D-galactosamine and sialic acid, but it can also bind to non-saccharide ligands, such as N-acetyl cysteine, N-acetylglycine, acetylcholine, elastin and some corticosteroids, as well as the oxidized and acetylated form of LDL, or DNA (Matsushita, 2007; Thiel, 2007; Runza, Schwaeble et al., 2008; Garred, Honore et al., 2009; Garred et al., 2010; Matsushita, 2010). It has been demonstrated that ficolin L recognizes some of the lipopolysaccharides, capsular polysaccharides, â-1-3-D-glucans of fungi and lipoteichoic acids. Therefore it binds to certain strains of *S. enterica* and *E. coli*, but primarily to saphylococci and streptococci: *Staphylococcus aureus, Streptococcus pneumoniae, S. pyogenes* and *S. agalactiae* (Matsushita, 2007). Probably, binding to the beta-haemolytic streptococci of Group B (*Streptococcus agalactiae*), is especially important, as these bacteria are the most common cause of meningitis and sepsis in neonates. Among the ligands for this lectin, the trisaccharides and tetrasaccharides, containing the terminal LacNAc-(β-Gal [3-O—SO$_3$] [6-O—SO$_3$]-(1→4)-β-GlcNAc-carrier) or GlcNAc, heparin (its fibrinogenic domain) and highly-sulphated glycosaminoglycans have also been described (Gout, Garlatti et al., 2009).

Ficolin H (also known as ficolin 3 or Hakata antigen, initially described as thermolabile β2 macroglobulin) is synthesized in hepatocytes, epithelial cells of the bile ducts, for alveolar cells of type II, the bronchial epithelium and the glial cells. The low level of expression was found in the cells of heart, kidneys, pancreas, spleen, and placenta. The protein is released to the blood, bile ducts and the mucus covering the respiratory tracts. Because the amount of ficolin H synthesized in lungs is higher than that in the liver, probably this lectin can be attributed not only to systemic (as released to the blood), but also to local protective role in the respiratory tract. Its concentration in sera of healthy adult humans is relatively high. According to the original, widely cited work (Yae et al., 1991) it ranges from 7 to 23 µg/ml (on average, approximately 18 µg/ml). The latest data published by Andersen and co-workers (Andersen et al., 2009) indicate that it may be even higher (on average above 32 µg/ml, in the range from 10 to more than 80 µg/ml). Among the ficolin-3 (H) ligands, the polysaccharide isolated from the bacterium *Aerococcus viridans* 86965 (probably a capsular polysaccharide) (Tetta et al., 1998; Matsushita et al., 2002), BSA-NAc (Lacroix et al., 2009; Munthe-Fog et al., 2009), BSA-Gal, D-fucose and D-Galactose (Gout, Garlatti et al., 2009), the surface antigens of lymphoma cell line T-lymphocytes (Jurkat cell line) were identified (Gout, Garlatti et al., 2009).

As demonstrated in agglutination tests and in the agglutination inhibition assays of human erythrocytes (Sugimoto, Yae et al., 1998), ficolin-3 binds to the LPS of *Salmonella Minnesota* and *Typhimurium* as well as *E. coli*. The above cited research of Gout and co-workers (Gout, Garlatti et al., 2009) shows the most precise attempts to determine the specificity of the ficolins towards saccharide ligands. In the study, matrices (glyco-arrays), containing the 377 related glycans were used. The queried glycans, both naturally occurring and synthetic, comprised mainly the structures derived from mammalian cells.

As shown, the specificity of ficolin-3 (H) towards ligands is very poorly characterized. In addition, concerning the sequence of amino acids, the ficolin-3 (H) substantially differs from other ficolins, showing only 45% homology in relation to ficolin-1 and -2 and 58% homology within the FGB domain. As for the different types of synthetic compounds, it has been shown recently, that ficolin-3 also binds to the BSA-NAc (Munthe-Fog, Hummelshoj et al., 2009). BSA-NAc ligand was used in the cited research for induction of the lectin pathway activation by human serum. The interaction of ficolin-3 with both the BSA-NAc and bacteria of *A. viridans* 86965 and their polysaccharide have not been characterized on the molecular level (Tsujimura et al., 2002). As already mentioned, the specificity of ficolins is very poorly known and currently disputes continue about the nature of the chemical ligands they recognize. The chemical structures of some PAMP's, or the presence of specific antibodies in the blood justifies the assumption that they may activate the complement system simultaneously through all the pathways: the classical pathway, the lectin pathway and the alternative pathway. In addition, these activation pathways of the complement system are co-dependent at certain stages. So far an amplification mechanism of the classical and lectin pathways through the activation of the alternative pathway has been described (Degn, Hansen et al., 2009).

Research aimed at elucidating of the mechanisms underlying these processes carried out in vitro, in vivo or using the isolated model systems of ligand-protein type requires the vast repertoire of experimental tools that would allow for an isolation and purification of key proteins, detection of their level in bodily fluids and tests of their activity, using the immunochemical methods and blocking their activity. As in most of the studies on mechanisms of the immune system, the complement constitutes a complex system as far as the research techniques are concerned.

Currently the emphasis is on obtaining such experimental tools that enable examination of various ways of complement activation independently, under conditions that are similar to physiological (Herpers et al., 2009; Inoshita et al., 2009). The selection of an adequate ligand is essential in these tests and this task is extremely difficult in case of ficolins due to the lack of relevant data. A conjugate of BSA-NAc has been described and used for such purposes as a ligand for ficolin-3 (H). However, it does not occur in nature, and was obtained as a result of chemical synthesis.

Determination of the ficolin level, activity and the ability to activate the complement system is important regarding the diagnosis and characterization of the immunodeficiencies concerning the complement and is often related to polymorphisms within genes coding the lectin. As demonstrated by the fairly well characterized example of human MBL, the effects of the mutation may include disruption of the structure and function, a shorter half-life and a reduced concentration in serum. For MBL, the consequences of these deficiencies are particularly serious in people with an immature or malfunctioning immune system and most often they include increased susceptibility to infection (sometimes life-threatening). It can be assumed that as a result of further research into the importance of ficolins, their role in immune response and clinical effects associated with their deficiency will be explained and documented. For example, the published data on the potential risks, which may be the result of the ficolin-2 (L) deficiency, are still very scarce. A higher prevalence of this deficiency (defined quantitatively) has been observed in women, with recurrences of spontaneous miscarriages (Kilpatrick et al., 1999). Significantly lower concentrations of ficolin L was observed also in pregnant women with the preeclamptic condition, as compared with the healthy pregnant women (Wang et al., 2007). The study of single nucleotide polymorphisms of the gene encoding the ficolin-2—FCN2 and the concentration of the protein may be a useful diagnostic tool in future. In children with deficiencies of ficolin L significantly more mutations are present at positions 64 and 6424 than in children with high concentrations of the protein. On the contrary, the frequency of variant alleles of pair −4 and 6359, is substantially lower in children with deficiencies of ficolin L (Cedzynski et al., 2007). There was also a higher prevalence of quantitative ficolin L deficiency in children with recurring respiratory infections accompanied by asthma and allergic rhinitis, as compared with healthy children (but not among the children with recurring infections and allergic diseases excluded) (Atkinson et al., 2004; Cedzynski et al., 2009).

It has been demonstrated that the ficolin L deficiency increases the risk of premature birth, low birth-weight and birth-related infections (Swierzko et al., 2009). Knowledge of the physiological role of ficolin H and the clinical significance of its deficiencies is scarce. Significantly lower concentrations of this lectin in persons with sarcoidosis have been demonstrated in comparison with control group (Svendsen et al., 2008). Attempts to tell whether the deficiency of this factor affects the risk of a disease outbreak, or whether illness affects the regulation of FCN3 gene expression or active protein is consumed, have failed. Lower concentrations of ficolin H are also present in patients with systemic lupus erythematosus, and as mentioned before, are related to the production of autoantibodies directed against this protein, rather than a genetically determined disruptions of synthesis (Yae, Inaba et al., 1991; Andersen, Munthe-Fog et al., 2009). Serum concentration of ficolin H rockets during pregnancy, which may suggest its important protective role. However, as mentioned above, significantly lower concentrations of ficolin L were observed in preeclamptic pregnant women, as compared with healthy pregnant women. In syncytiotrophoblasts from the placenta of ill women, significant quantities of ficolin H are detected, that are presumably related to the local inflammatory process, and indicate the likely involvement of the protein in pathology (Wang, Yim et al., 2007). Recently, Schlapbach and co-workers have demonstrated that low concentrations of ficolin H in the serum of children undergoing anticancer chemotherapy increase the risk of neutropenic fever and sepsis (Schlapbach et al., 2009). Fukutomi and co-workers observed that the concentration of ficolin H is also reduced with the onset of cirrhosis of the liver, therefore its concentration can be a diagnostic marker, indicating the level of dysfunction of this organ (Fukutomi et al., 1996).

Treatment of certain immunodeficiencies is based on delivering (substitution) of the corresponding factor obtained from healthy donors or its recombinant form. Recombinant or native MBL protein is currently in clinical trials as a potential drug in cases of deficiencies of this lectin.

The starting point for diagnosing deficiency, monitoring the therapy of such deficiencies, as well as explaining their mechanisms are methods for the determination of the concentration and activity in bodily fluids. The first step for the treatment of this type of deficiency is also to get active, purified preparations of their native or recombinant forms.

For ficolin-3, two methods are mainly used for the determination of the concentration of this protein in bodily fluids. One of them ("sandwich" ELISA) is based on the use of monoclonal antibodies against human ficolin-3 (H) used both as the so-called capturing antibody and the detecting antibody for detection of proteins. The second method employs bovine albumin that is chemically modified by N-acetylation (BSA-NAc). Currently, there is a commercially available test manufactured by Hycult company that allows for determination of the total concentration of ficolin-3 (H) using "sandwich" ELISA. As for the second method, that is this using BSA-NAc conjugate as a ligand, the possible implementation of the method in evaluation of activities of the ficolin-3-MASP complexes has been reported recently (Munthe-Fog, Hummelshoj et al., 2009).

The first method enables determination the serum level of the protein, which does not necessarily correlate with the active form of ficolin-3. The second method is distinguished by poorly described molecular mechanism of interaction of ficolin-3 (H) with N-acetyl groups. Additionally, the BSA-NAc is not naturally occurring ligand.

The gol of the present invention is to provide ligands, which specifically bind to ficolin-3 and activity thereof which could be used to determine the concentration of active forms of ficolin-3 and activity thereof. Unexpectedly, this goal was achieved in the present invention.

The subject according to the present invention is a polysaccharide with an affinity for ficolin-3 or a derivative thereof, characterized in that its structure is described by general formula:

$$PD_t\text{-}(PD)_n\text{-}[Hep]\text{-}Kdo$$

wherein:

n is an integer from 0 to 100, preferably less than 50, more preferably less than 40, and in the case of polysaccharides of bacterial origin usually less than 30, $PD_t$ stands for:

the repeating oligosaccharide unit $PD1_t$ of the formula:

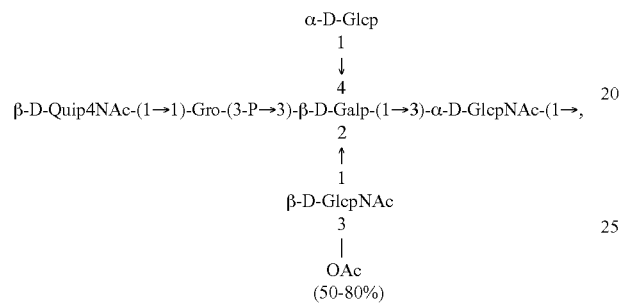

the repeating oligosaccharide unit $PD2_t$ of the formula:

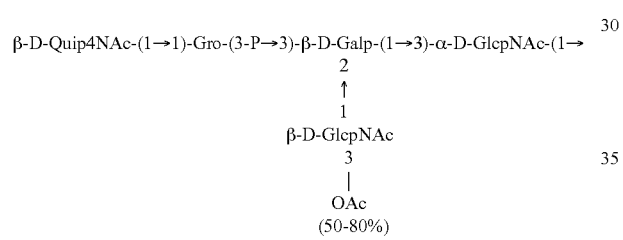

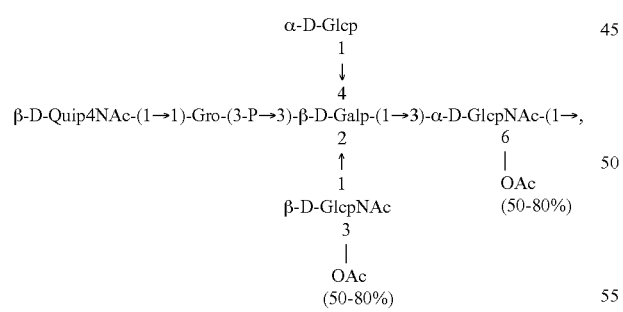

the repeating oligosaccharide unit PD3t of the formula:

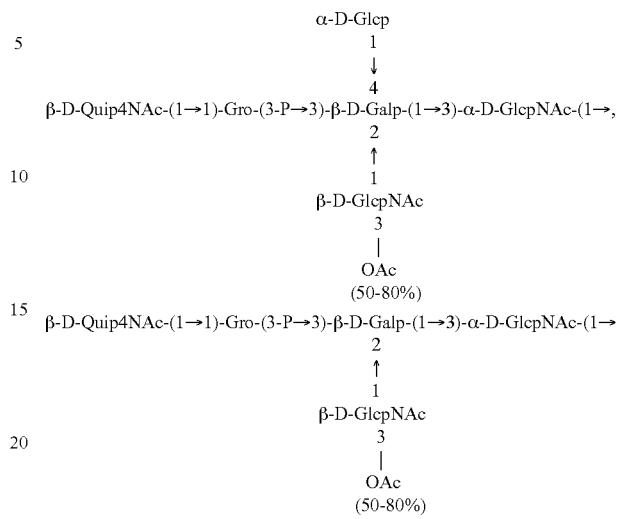

PD stands for:

the repeating oligosaccharide unit PD1 of the formula:

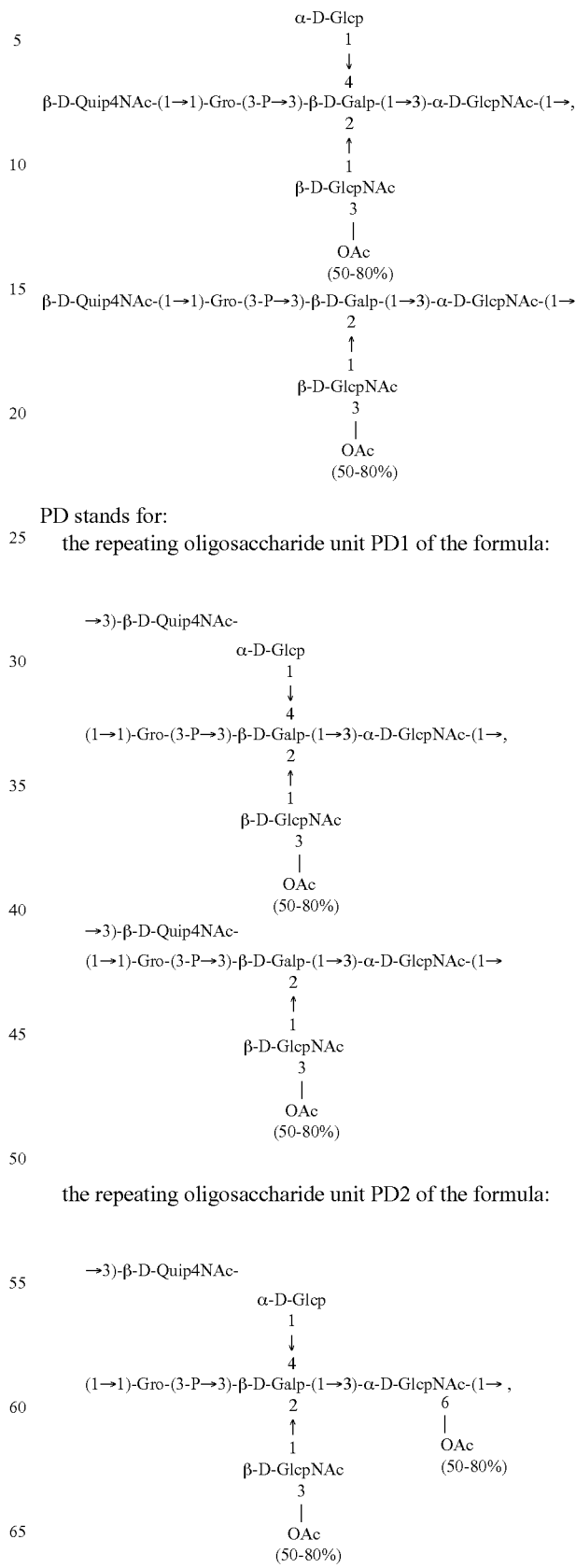

the repeating oligosaccharide unit PD2 of the formula:

-continued

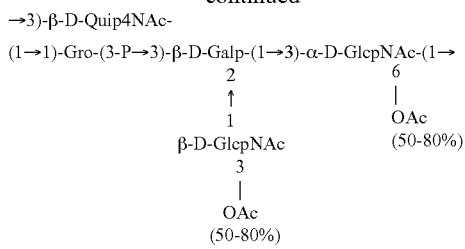

or
the repeating oligosaccharide unit PD3 of the formula:

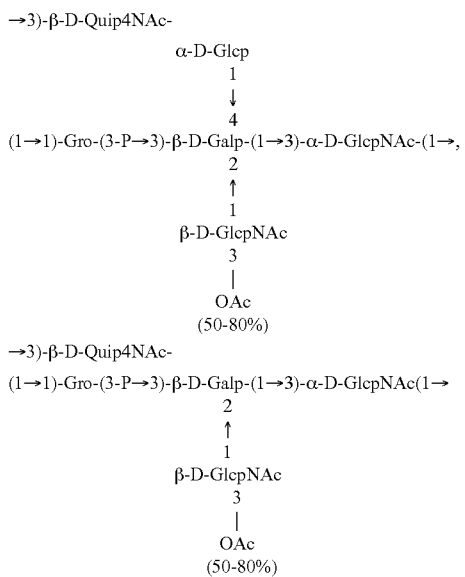

[Hep]-Kdo stands for the disaccharide of the formula:

L-α-D-Hepp
1
↓
8
→7)-Kdo

Preferably, the polysaccharide according to the present invention is characterized in that it comprises compounds selected from polysaccharides of the general formula:

PD1$_t$-PD1-[Hep]-Kdo, PD2$_t$-PD2-[Hep]-Kdo or PD3$_t$-PD3-[Hep]-Kdo.

Equally preferable is a derivative of the polysaccharide according to the present invention, which is characterized in that it is selected from the group comprising reduced polysaccharide PDt-(PD)n-[Hep]-Kdo, a conjugate thereof with a known carrier protein, or with chromatography medium.

According to the present invention, the phrase "reduced polysaccharide PDt-(PD)n-[Hep]-Kdo" represents a compound in which a Kdo residue is present in a form of linear polyalcohol, 1-carboxy-3-deoxyoctitol, with a carboxyl and deoxy group substituting the first and the third carbon atom, respectively This derivative is a result of reduction, especially with the use of sodium borohydride.

Known carrier proteins to be used for preparation of the conjugate according to the present invention can be vertebrate serum albumin, egg albumin.

Known chromatographic media that can be used to obtain the conjugate according to the present invention are preferably the modified agarose, cellulose or polyacrylamide.

The invention further provides a method for the preparation of the polysaccharides and derivatives thereof with an affinity for ficolin-3, characterized in that:
a) bacterial lipopolysaccharide is isolated, preferably from a strain of *H. alvei*,
b) the obtained lipopolysaccharide is degraded and a polysaccharide fraction is separated,
c) the polysaccharide fraction containing polysaccharides which are built of repeating units with molecular weight ranging from 2400 kDa to 26000 kDa is isolated,
d) alternatively, the obtained polysaccharides are reduced, particularly in the presence of NaBH$_4$, and preferably conjugated with a known carrier protein or chromatography medium.

Preferably, the method according to the invention is characterized in that, a culture of *H. alvei* strain is carried out in step (a) and this *H. alvei* strain is selected from strains: *H. alvei* 981, 1200, 1203, 1205, and 1208. These strains were deposited on Jun. 7, 2010 with the Polish Collection of Microorganisms (Institute of Immunology and Experimental Therapy, Polish Academy of Sciences, Wroclaw), acting in conformity with the Budapest Treaty, under accession numbers presented in the following Table:

| Strain | Deposit no. at the Polish Collection of Microorganisms (PCM) |
| --- | --- |
| *H. alvei* 981 | B/00030 |
| *H. alvei* 1200 | B/00031 |
| *H. alvei* 1203 | B/00032 |
| *H. alvei* 1205 | B/00033 |
| *H. alvei* 1208 | B/00034 |

Preferably, the method according to the present invention is characterized in that, the extraction of lipopolysaccharide from the bacterial mass is carried out in step (a) for approximately 15 min at approximately 65° C., in aqueous solution of phenol, preferably phenol solution at a concentration of approximately 45%, followed by recovering of the lipopolysaccharide from separated aqueous phase.

Preferably, the method according to the present invention is characterized in that the separated polysaccharide is hydrolysed in step (b) in approximately 1-1.5% solution of acetic acid, for approximately 15 to 60 min at temperature of 100° C.

Preferably, the method according to the present invention is characterized in that the polysaccharide fraction is fractionated with the use of chromatography in step (c) in order to separate the O-specific chains from the shorter chains of polysaccharides and core oligosaccharides, wherein the chromatography is preferably performed on a column filled with polyacrylamide gel, such as commercially available Bio-Gel P-10, equilibrated with a buffer containing 0.05 M pyridine/acetic acid/water in 10/4/986 ratio, with pH of approximately 5.6.

Preferably, the method according to the present invention is characterized in that the obtained polysaccharides are reduced and conjugated to the carrier protein in step (d), wherein such carrier protein may be particularly a bovine serum albumin or chromatography medium, and particularly preferable is a modified agarose such as commercially available Sepharose®.

Another aspect of the invention is the use of the bacterial lipopolysaccharide or the polysaccharide contained therein or their derivative as a ligand for ficolin-3, especially for purification or detection of ficolin-3 or its derivatives.

As used herein, the term "ficolin-3" or "its derivatives" refers to human ficolin-3, which may be a natural protein or a protein obtained by artificial means, particularly recombinant protein, including possible mutants and other derivatives having essentially the activity of natural ficolin-3.

Preferably, the use according to the invention is characterized in that the lipopolysaccharide obtained from strains: *H. alvei* 981, 1200, 1203, 1205, 1208 or the polysaccharide contained therein or a derivative thereof is used. As described above, all strains related to this application were deposited with the PCM.

Preferably, the use according to the invention is characterized in that the polysaccharide or its derivative according to the present invention is used, which are defined above or obtained by the method according to the invention as described above.

Preferably, the use according to the invention is characterized in that the ficolin-3 derivative is a complex of ficolin-3 with serum or plasma-derived serine proteases, MASP.

Further preferred use according to the invention is characterized in that the detection is carried out to determine an activity and/or level of ficolin-3 or its derivatives in the serum or other bodily fluids.

Further preferable use according to the invention is characterized in that the purification is carried out in order to obtain serum or plasma devoid of the ficolin-3.

It should be mentioned at the beginning of the detailed description of the selected preferable embodiments according to the present invention, that the starting point for the present invention was the discovery, during a dot-blot analysis, of strong interaction between human ficolin-3 (H) and bacterial lipopolysaccharides, particularly LPS isolated from strains of *H. alvei* 2, 23, 37, 38, 981, 1200, 1203, 1205, and 1208. The LPS-ficolin pair is another example of the key interaction, which is important for innate immunity. Lipopolysaccharide (LPS) constitutes one of the molecular patterns PAMP as well as the main surface antigen and virulence factor of Gram-negative bacteria, and the ficolin-3 (H) constitutes a component of the complement system (key mechanism of innate immunity), which binds LPS and activates the complement cascade through the lectin pathway.

During investigations leading to the present invention, the inventors have identified and isolated bacterial ligands, which specifically and strongly bind inter alia to human ficolin-3 (H). In a preferred embodiment of the present invention, the ligands are polysaccharide fragments of *H. alvei* lipopolysaccharides, which are obtained by chemical degradation of lipopolysaccharide. Nine LPS consisting of regions bound by human ficolin-3 (H) have been identified as a result of screening of *H. alvei* lipopolysaccharides: LPS of *H. alvei* 2, 23, 37, 38, 981, 1200, 1203, 1205, and 1208. Complete structures of these lipopolysaccharides have not been identified and published to date. The only data available was relate to the structures of repeating units of the O-specific chains present in LPS 2, 23, 38, 1200, 1203, 1205, 1208 (Gamian et al., 1991, Katzenellenbogen et al., 1992, Katzenellenbogen et al., 1999; Dag et al., 2004). These structures were determined with the use of instrumental and chemical analysis of high molecular-weight fractions of the O-specific polysaccharides, having the number of repeating units greater than or equal to 4. Such fractions were obtained by acid hydrolysis of lipopolysaccharide in the presence of detergent (1.5% $CH_3COOH$, 2% SDS) for 15 min at 100° C. These conditions resulted in hydrolysis of acid labile ketosidic bond present between the lipid A and the sugar part of LPS (the core oligosaccharide substituted by the O-specific chain). After separation of lipid A, the obtained mixture of poly- and oligosaccharides was fractionated with the use of gel filtration chromatography. Taking into account the current knowledge about the general structure of enterobacterial lipopolysaccharides, the presence of a glycosidic bond between the core oligosaccharide and the O-specific chain, which is non-degradable under these conditions, should generally result in products, containing the core oligosaccharide and polysaccharide fractions built of the core oligosaccharide substituted with different number of repeating units of the O-specific chain. In the ongoing investigation on lipopolysaccharides of *H. alvei* leading to the present invention, the inventors have identified the unusual structural element, in comparison with the known enterobacterial LPS, the presence of KdoII residue in the distal region of the core oligosaccharide (Lukasiewicz et al., 2009). Fragment of *H. alvei* 32 LPS, which contained a sugar portion of the lipid A substituted with core oligosaccharide terminated with trisaccharide fragment L-α-D-Hepp-(1→4)-[α-D-Galp6OAc-(1→7)]-α-Kdop-(2→] was isolated. The presence of two Kdo regions within the LPS molecule substantially modifies the composition of the mixture of poly- and oligosaccharides obtained from acid hydrolysis of LPS. For *H. alvei* LPS, the hydrolysis of the ketosidic bond occurs at two positions: (i) between lipid A and KdoI residue, which substitutes the lipid A, and (ii) between KdoII residue present in the outer core oligosaccharide region and the remaining part of the core region. In the case of lipopolysaccharide, whose fragments represent a subject of one of the aspects of the present invention, it has been demonstrated that the KdoII residue is a place of substitution for the O-specific chain. Therefore, it was possible to obtain polysaccharides devoid of almost an entire core region with the Hep-Kdo motif at their reducing ends as a result of acid hydrolysis of *H. alvei* LPS 23, 1200, 1203, and 1205. Thus this report constitutes the first disclosure of the presence of this element in the O-specific polysaccharide fractions isolated from LPS of *H. alvei* 1200, 1203 and 1205. These polysaccharides are built of one, two and more carbohydrate repeating units. Moreover, the present invention is the first report about a structure of the biological repeating unit of the O-specific polysaccharide of *H. alvei* LPS 1200, 1203, and 1205. Regarding the structural analysis of the repeating units of the O-specific chains of *H. alvei* LPS, the structural element Hep-Kdo described herein has not been identified in the previously cited publications (Jachymek et al. 1995; Sunday et al., 1996, Petersson et al., 1997; Jachymek et al., 1999, Dag et al., 2004). These analyses were performed for fractions containing polymers with a number of repeating units greater than 4-5. The Hep-Kdo motif was not identified due to predominance of the repeating unit components. The fragment of the O-specific chain containing from 4 to 8 sugar residues characteristic for the O-specific chain and the Hep-Kdo disaccharide at the reducing end was isolated only in the case of LPS of *H. alvei* 2 (Gamian, Romanowska et al., 1991). Examples of ficolin-3 ligands disclosed in this application are polysaccharide fragments of *H. alvei* lipopolysaccharides 1200, 1203, 1205, particularly LPS 1200, which are obtained by chemical degradation of the lipopolysaccharide. These polysaccharides have a structure of the general formulas:

$PS1:PD1_r\text{-}(PD1)_n\text{-}[Hep]\text{-}Kdo,$ $PS2:PD2_r\text{-}(PD2)_n\text{-}[Hep]\text{-}Kdo,$ $PS3:PD3_r\text{-}(PD3)_n\text{-}[Hep]\text{-}Kdo,$ wherein the symbol PD stands for a subunit of the O-specific chains isolated from *H. alvei* 1200 (PD1), 1203 (PD2) and 1205 (PD3) lipopolysaccharides, respectively.

Figure 1B:
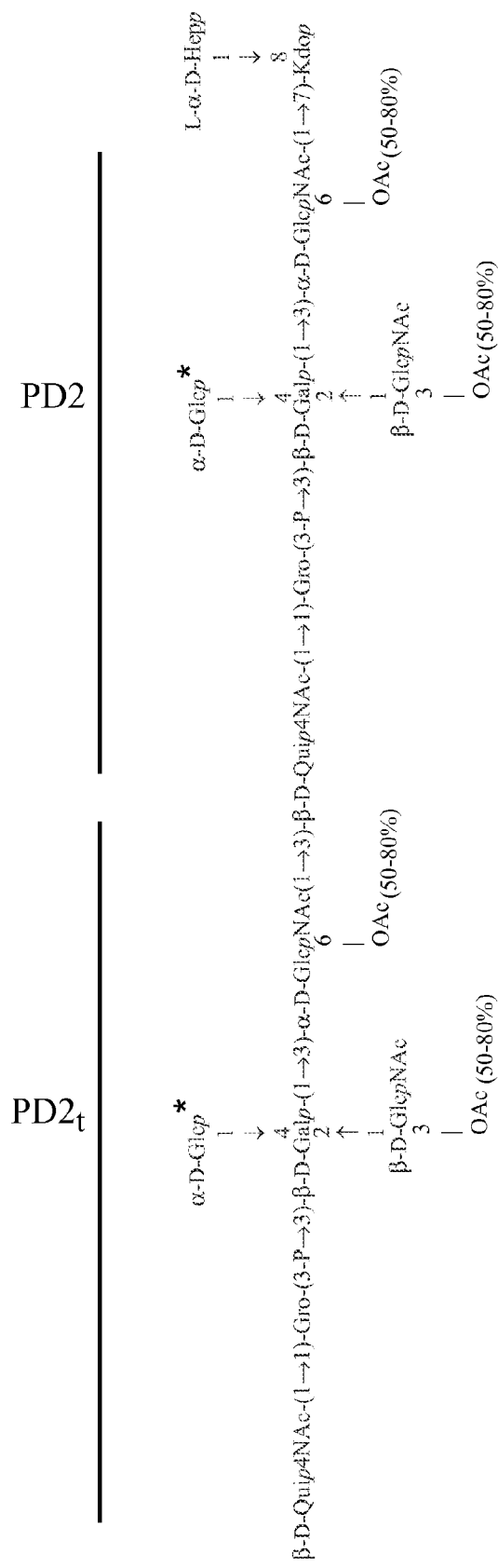
Figure 1C:
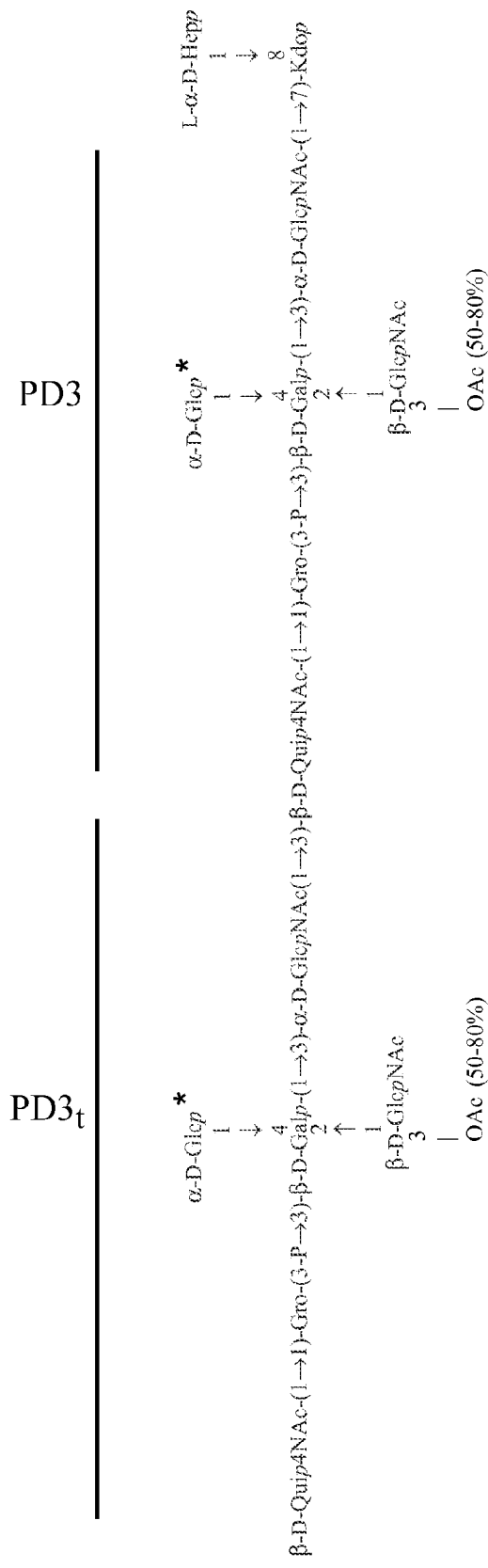

Moreover, all the polysaccharides are additionally O-acetylated (FIG. 1). The number n is an integer greater than or equal to 0. The disaccharide, which is marked with "[Hep]-Kdo" symbol has a following structure: →7)-[L-glycero-D-manno-Hep-(1→8)-]-Kdo. Regardless of repeating unit type (PD1 or PD2 or PD3), this disaccharide is substituted at position 7 of the Kdo residue by the first residue of the O-specific chain repeating unit. →3)-α-D-GlcpNAc is the first residue in the case of PD1, PD2, PD3. The structures of fragments PD1$_t$-(PD1)$_n$-[Hep]-Kdo (n=1), PD2$_t$-(PD2)$_n$-[Hep]-Kdo (n=1), PD3$_t$-(PD3)$_n$-[Hep]-Kdo (n=1) are shown in FIG. 1. Symbols PD1$_t$, PD2$_t$ and PD3$_t$ stand for the terminal repeating units present at a non-reducing end of each polysaccharide. In the case of PD1$_t$, PD2$_t$ and PD3$_t$, β-D-Quip4NAc-(1→ is a terminal sugar at the non-reducing end of the terminal subunit. All the polysaccharides described herein (PS1, PS2 and PS3) are obtained by chemical degradation of lipopolysaccharides. PS1 is obtained by chemical degradation of the lipopolysaccharide isolated from *H. alvei* 1200 (Example 5). PS2 is obtained by chemical degradation of the LPS isolated from *H. alvei* 1203. PS3 is obtained by chemical degradation of the LPS isolated from *H. alvei* 1205. The polysaccharide fraction may contain one or more repeating units of the O-specific chain. The polysaccharide PS1 and the reduced form thereof, which were used in examples presented in the experimental section, contained at least four repeating units of the O-specific chain.

One aspect of the invention also relates to the reduced polysaccharides. In one preferred embodiment it relates to PS1$_{red}$, PS2$_{red}$, PS3$_{red}$, that maintain structural features enabled the binding of human ficolin-3 and recombinant form thereof. In comparison with the native polysaccharides, the reduced polysaccharides are characterized by the presence of a poly-hydroxy-3-deoxyoctonic acid at the reducing end as a result of Kdo reduction. Reduction of polysaccharides is carried out with the use of NaBH$_4$. The obtained product is purified by gel permeation chromatography. An example of preparation of the reduced polysaccharides was described in details in the experimental section (Example 6).

Another aspect of the invention relates to the use of the reduced polysaccharides according to the invention, particularly PS1$_{red}$, PS2$_{red}$ and PS3$_{red}$, as ligands for human ficolin-3 and recombinant forms thereof, other components of the complement system and recombinant forms thereof with specificity similar to the specificity of ficolin-3, and proteins of the complement system derived from other organisms and having similar specificity and in vitro and in vivo activators of the complement system. Especially preferred is the use of these molecules as ligands excluding the interaction of these polysaccharides with MBL, ficolin-L, ficolin-M, and IgG.

Another aspect of the invention relates to covalent conjugates of polysaccharides of the invention, preferably PS1$_{red}$, PS2$_{red}$ and PS3$_{red}$, with carrier proteins such as, for example BSA and other carriers that may be used for the immobilization of polysaccharides on solid supports such as the surface of the ELISA plate. The preparation of the exemplary conjugate of PS1$_{red}$ with BSA (PS1200-BSA) was described in details in the experimental section (Example 7).

It was shown that conjugates of this type can be an element of a functional diagnostic test, the test for a measurement of the concentration and the test for the selective measurement of ficolin-3/MASP-2 complexes activity in serum and other bodily fluids, as well as for the detection of complexes of recombinant forms of ficolin-3. An example of the use of the conjugates was described in details in the experimental section. Example 9 describes an ELISA assay for binding detection of recombinant ficolin-3 (H) to lipopolysaccharide of *H. alvei* 1200 and PS1200-BSA conjugate. Example 10 presents a comparison of the binding of serum-derived ficolin-3, -2, -1, MBL and natural immunoglobulins to different ligands (BSA, BSA-Ac, LPS 1200 and PS1200-BSA) with the use of a buffer containing Hepes buffer or a high ionic strength buffer. Example 11 describes a comparison of the serum-derived ficolin-3 (H) detection performed with the use of ELISA and the PS1200-BSA ligand with the method of "sandwich" type.

Examples 12 and 13 describe the detection of ficolin-3 concentrations and ficolin-3\MASP-2 complexes activity in healthy adult donors with the use of ELISA and PS1200-BSA ligand, respectively. Anyone skilled in the art can assume on the basis of available information that the conjugates of the invention may be an element of a functional diagnostic test for selective measurement of the activity of ficolin-3/MASP-1 complexes, ficolin-3/MASP-3 complexes and complexes of ficolin-3 with any other factor or factors modulating the activity of ficolin-3 and homologues and/or analogues thereof, and complexes of similar type, which are formed with recombinant forms of ficolin-3, analogues and/or homologues thereof.

Another aspect according to the present invention relates to covalent conjugates of polysaccharides according to the present invention, particularly PS1$_{red}$, PS2$_{red}$ and PS3$_{red}$, with carriers other than proteins such carriers that can be used for the immobilization of the reduced polysaccharides on solid carriers, which can be further used as ligands for ficolin-3 and homologues and/or analogues thereof, recombinant ficolin-3 and homologs and analogues thereof or complexes of similar type, which are formed with recombinant forms of ficolin-3 and recombinant forms of analogues and homologs of ficolin-3 in ELISA assays, immunoblotting, methods for purification of ficolin-3 from serum and other bodily fluids and methods for preparation of serum-free ficolin-3 based on affinity chromatography. Such a carrier to prepare said conjugates for affinity chromatography purposes may be modified agarose, cellulose or polyacrylamide, for example commercially available media SEPHAROSE® 4B (Example 8).

Such conjugates can also be used in affinity chromatography to prepare a serum/plasma or other bodily fluids devoid of ficolin-3 (H).

A special embodiment of the invention relates to the use of polysaccharides isolated from the LPS isolated from other *H. alvei* strains, which were bound by ficolin-3 in the dot-blot assay (Example 1) for the purposes described above. Such polysaccharides comprise these isolated from the LPS of *H. alvei* 2, 23, 37, 38, 981, and 1208.

Figure 2:
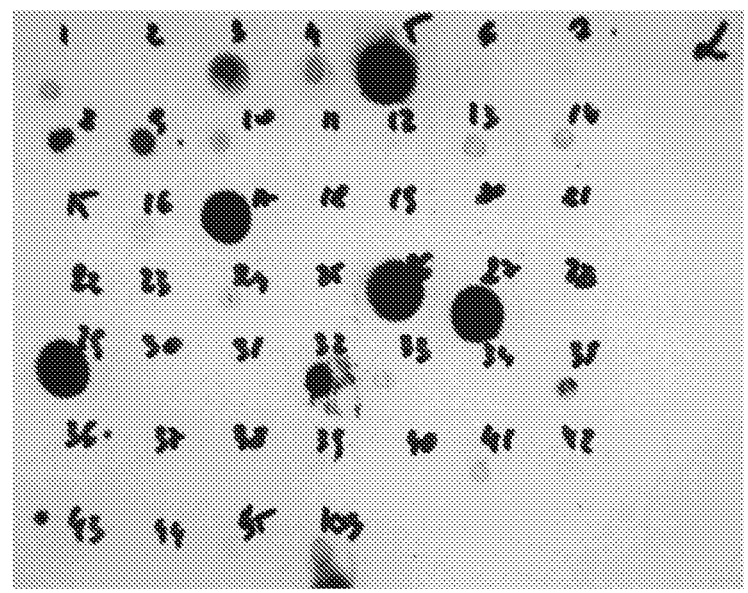
Figure 3:
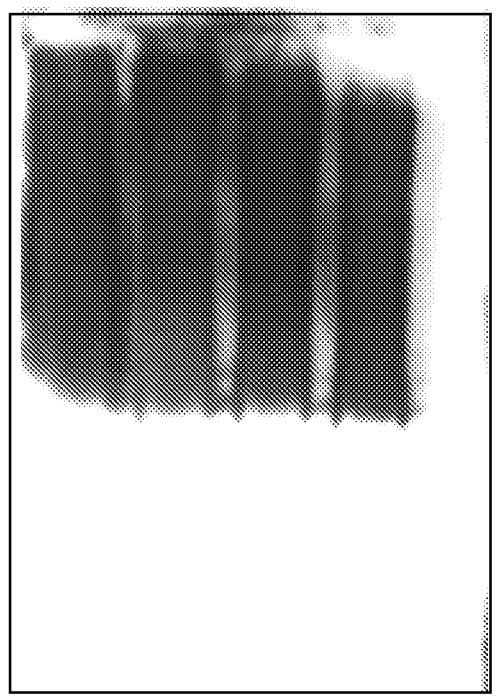
Figure 4:
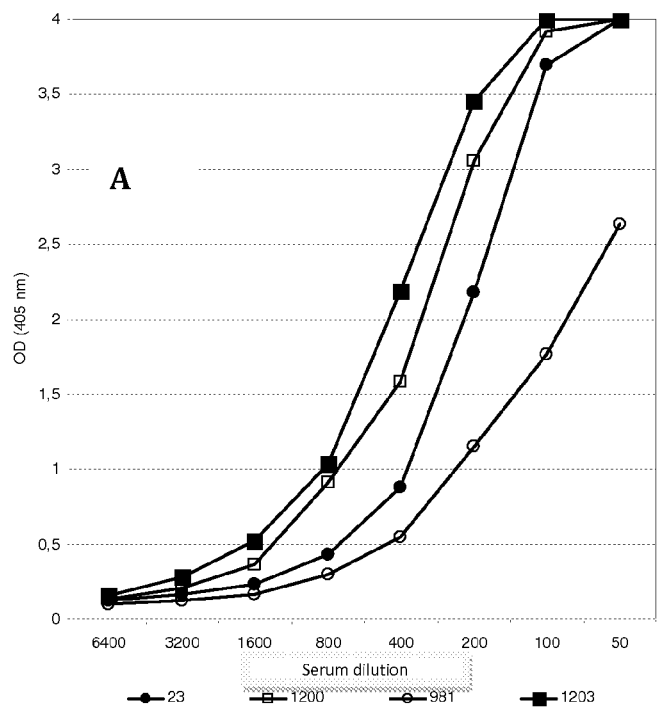
Figure 4:
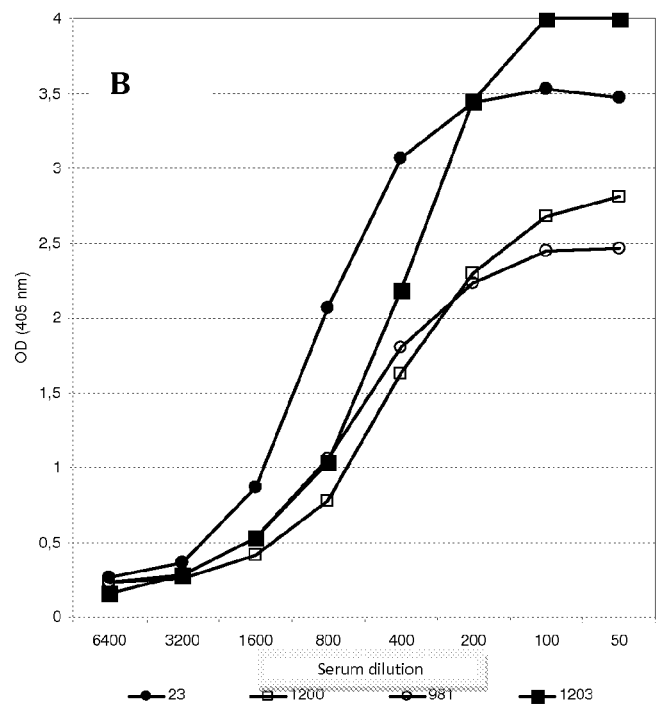
Figure 5:
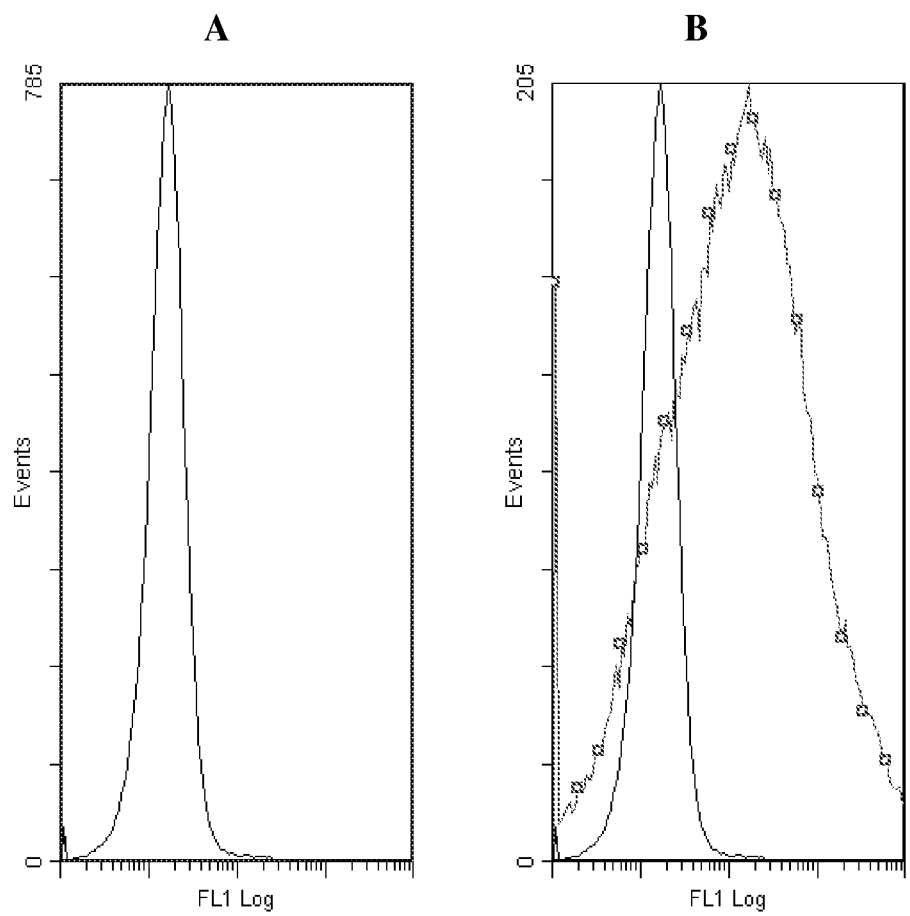
Figure 6:
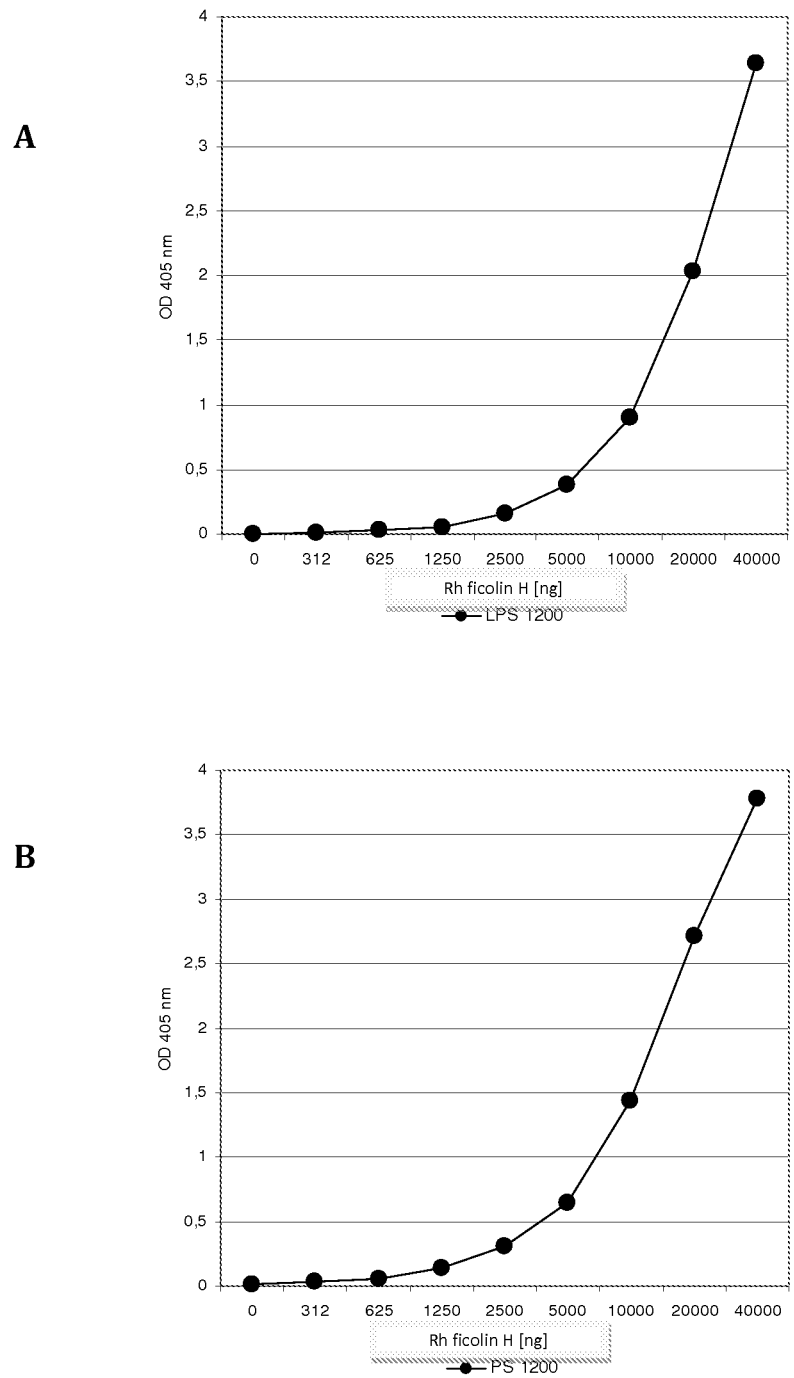
Figure 7:
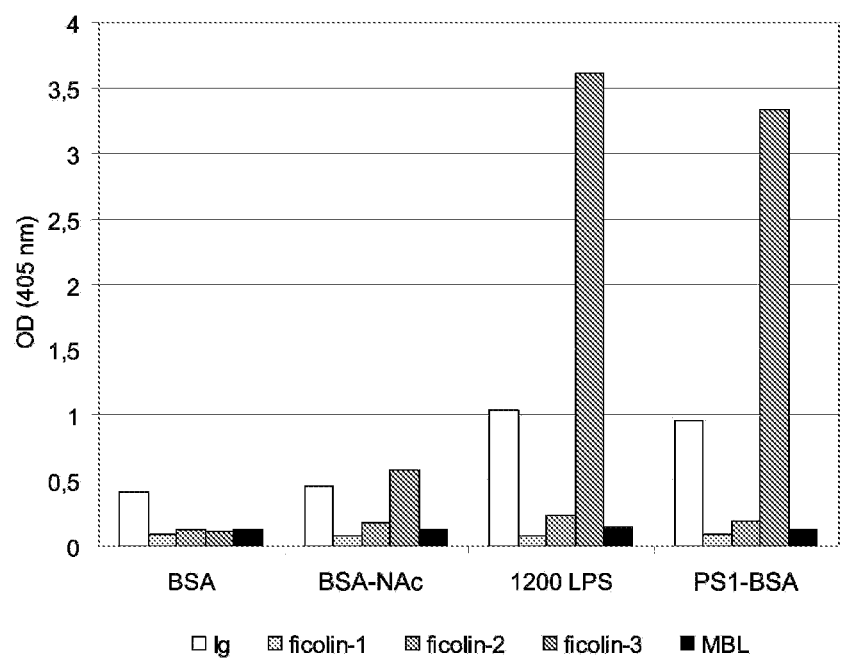
Figure 8:
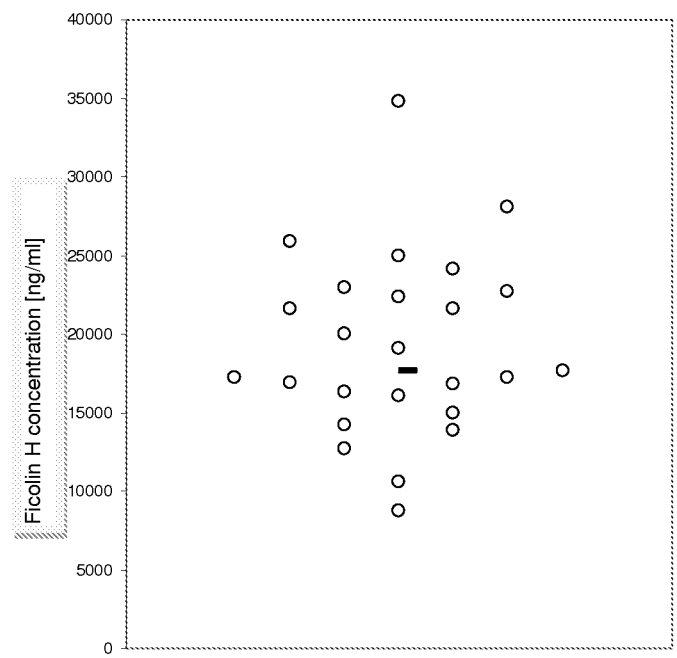
Figure 9:
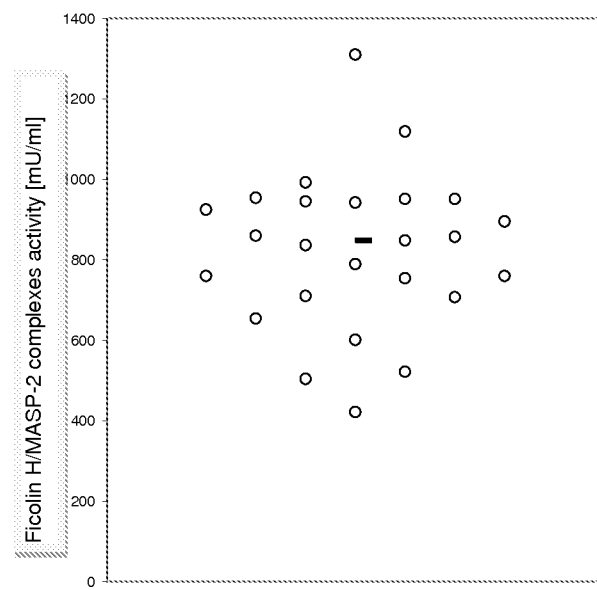

Further properties of the invention are described in a more detailed way in the following examples and are supported by the experimental results described in the included figures. FIG. 1 shows polysaccharide structures PD1t-PD1-[Hep]-Kdo, PD2t-PD2-[Hep]-Kdo, PD3t-PD3-[Hep]-Kdo isolated from LPSs of *H. alvei* 1200, 1203, 1205, respectively. FIG. 2 presents the reaction of the human ficolin-3 (H) with the lipopolysaccharides of the selected strains of *H. alvei* in the dot-blotting. LPSs presented are in the following order: (1) LPS *H. alvei* 1, (2) LPS 1M, (3) LPS 2, (4) LPS 17, (5) LPS 23, (6) LPS 31, (7) LPS 32, (8) LPS 37, (9) LPS 38, (10) LPS 39, (11) LPS 399, (12) LPS 481, (13) LPS 600, (14) LPS 537, (15) LPS 744, (16) LPS 974, (17) LPS 981, (18) LPS 1187, (19) LPS 1188, (20) LPS 1190, (21) LPS 1191, (22) LPS 1192, (23) LPS 1195, (24) LPS 1196, (25) LPS 1198, (26) LPS 1200, (27) LPS 1203, (28) LPS 1204, (29) LPS 1205,

(30) LPS 1206, (31) LPS 1207, (32) LPS 1208, (33) LPS 1209, (34) LPS 1210, (35) LPS 1211, (36) LPS 1212, (37) LPS 1213, (38) LPS 1214, (39) LPS 1215, (40) LPS 1218, (41) LPS 1220, (42) LPS 1221, (43) LPS 1222, (44) LPS 1224, (45) LPS 114-60, (46) *K. pneumoniae* 03. FIG. 3 presents the reaction of the human ficolin-3 (H) with the electrophoretically separated (SDS-PAGE) LPS isolated from selected strains of *H. alvei* in Western blot. From the left: LPS 23, 1200, 1203, 1205, 1192. FIG. 4 demonstrates: (A) binding of the human ficolin-3 (H) by the lipopolysaccharides of the selected strains of *H. alvei* in ELISA (LPS 23, 1200, 981, 1203), (B) an activation of the ficolin H-MASP-2 complexes by the lipopolysaccharides of the selected strains of *H. alvei* in the ELISA (LPS 23, 1200, 981, 1203). FIG. 5 presents binding of recombinant H-ficolin to *H. alvei* 1200 bacteria in flow cytometry assay. FIG. 6 presents: (A) binding of recombinant H-ficolin to *H. alvei* 1200 in ELISA, (B) the binding of recombinant H-ficolin to *H. alvei* 1200-BSA in ELISA. FIG. 7 demonstrates the binding of the serum ficolin-3 (H), ficolin-2 (L), ficolin-1 (M), mannan binding lectin (MBL) and immunoglobulin to the bovine serum albumin, its acetylated derivative, lipopolysaccharide *H. alvei* 1200 and the polysaccharide of *H. alvei* 1200 conjugated with the BSA in buffer B1 (Munthe-Fog, Hummelshoj et al., 2009) and hypertonic buffer B2 (Petersen, Thiel et al., 2001). Human serum was diluted 1:50. FIG. 8 presents particular values of the concentrations of ficolin-3 (H) in human healthy adult donors. Black bar marks median (17622 ng/ml). The subject of the invention was ligand for ficolin-3 (H)—the high molecular weight polysaccharide isolated from lipopolysaccharide *H. alvei* 1200 conjugated with bovine albumin. FIG. 9 presents individual activity values of the complexes ficolin H-MASP-2 in human healthy adult donors. Black bar marks median (847 mU/ml). The subject of the invention was ligand for ficolin-3 (H)—the high molecular weight polysaccharide isolated from lipopolysaccharide *H. alvei* 1200 conjugated with bovine albumin. On the FIG. 10 correlation between the concentration of the ficolin-3 (H) and the activity of its complexes with MASP-2 (activation of the C4 element) in human healthy adults was presented. Trend line was marked. Ligand for ficolin-3 (H) was the high molecular weight polysaccharide isolated from lipopolysaccharide *H. alvei* 1200 conjugated with bovine albumin. R=0.683, p<0.0002.

Examples described below are for illustrative purposes only and it is obvious that these examples do not limit the scope of the invention in any way.

EXAMPLE 1

Binding of the Human Ficolin-3 (H) to the LPS of *H. Alvei* in Dot-Blotting

Lipopolysaccharides isolated from 45 different strains of *H. alvei* (1 mg/ml) were transferred onto PVDF membrane in the 3×5 µl volume. Membrane was incubated in turn with normal human serum (the source of ficolin-3), mouse monoclonal antibodies directed against ficolin-3 (H) (clone 4H5, HM2089, HyCult Biotechnology) and horseradish peroxidase-labelled rabbit anti-mouse Ig antibody (HRP) (DAKO). It was demonstrated that human ficolin-3 binds to the following LPSs isolated from *H. alvei*: 2, 23, 37, 38, 981, 1200, 1203, 1205, 1208 (FIG. 2).

EXAMPLE 2

Binding of the Human Ficolin-3 (H) to the LPS of *H. Alvei* in Immunoblotting

Studied lipopolysaccharides (LPS 23, 1200, 1203, 1205) were separated on 15% polyacrylamide gel and then transferred onto PVDF membrane. The membrane was incubated in turn with normal human serum (the source of ficolin-3), mouse monoclonal antibodies directed against ficolin-3 (H) (clone 4H5, HM2089, HyCult Biotechnology) and horseradish peroxidase-labelled rabbit anti-mouse Ig antibody (HRP) (DAKO). Analysis of the SDS-PAGE/Western-blot (FIG. 3) demonstrated that, the high molecular weight fractions of previously mentioned lipopolysaccharides, the O-specific polysaccharides, are responsible for the reaction.

EXAMPLE 3

The ELISA detecting binding of the ficolin-3 and complexes ficolin-3/MASP-2-dependent activation of the C4 element of the complement system by the *H. alvei* lipopolysaccharides. With the use of the ELISA test it was demonstrated that LPS *H. alvei* 23, 981, 1200 and 1203 not only bind the ficolin-3 but also activate the C4 element of the complement through the complexes of this lectin with MASP proteases in the antibody independent way (FIG. 4B). Microtiter MAX-ISORP® U96 plates (Nunc) were coated with lipopolysaccharides. Following the blocking step, assayed human serum (source of ficolin-3) was added in high NaCl concentration buffer (Petersen et al., 2001), in order to exclude activation of the complement via the classical pathway (antigen-antibody complex dependent). After incubation for 18 h at 4° C. binding of the ficolin-3 (H) with LPS was detected with the use of the specific monoclonal antibodies directed against ficolin-3 (H) (clone 4H5, HM2089, HyCult Biotechnology) and horseradish peroxidase-labelled rabbit anti-mouse immunoglobulin antibodies (FIG. 4A). Alternatively, the adequately diluted serum was added as a source of C4 factor to the induced ficolin-3/LPS complexes. After incubation for 2 h at 37° C., the bound C4 activation product was detected with the use of rabbit anti-human C4 antibody (Sigma) and HRP-labelled goat anti-rabbit immunoglobulins (Dako) (FIG. 4B).

EXAMPLE 4

An Estimation of Recombinant H-Ficolin 3 (H) Binding to the *H. Alvei* 1200 Cells in Flow Cytometry Assay

*H. alvei* 1200 bacterial cells, inactivated and fixed with formaldehyde were incubated with recombinant ficolin-3 (H), next the bound protein was detected with the use of selective mouse monoclonal antibodies followed by FITC conjugated mouse immunoglobulin specific antibodies (FIG. 5B). The reactivity was estimated using Cytomics FC 500 MPL Beckman-Coulter flow cytometer. Bacteria *H. alvei* PCM 1209, containing LPS that does not bind the ficolin-3 (H) were used as the control (FIG. 5B). With the use of flow cytometry it was also found that recombinant ficolin-3 (H) binds the surface structures of *H. alvei* strain 1200 cells (FIG. 5B), but not to the *H. alvei* 1209 (data not included).

EXAMPLE 5

Preparation Via Chemical Degradation and Structural Analysis of the Polysaccharide PS1 Isolated from *H. Alvei* 1200 LPS Preparation of the lipopolysaccharide from *H. alvei* strain 1200 was described by S. Dag and co-workers. (Dag, Niedziela et al., 2004). The bacteria were grown in liquid Davis medium at 37° C. After 48 h growth, bacteria were inactivated with 0.5% phenol and centrifuged using a CEPA flow laboratory centrifuge at speed of 39000 rpm and washed with 3 L of water. The obtained bacterial mass was suspended in water and freeze-dried. Lyophilised bacteria were thoroughly suspended in water (2 g/25 ml) followed by the addition of equal volume of 90% phenol. With thus obtained 45% phenol solution the lipopolysaccharides were extracted at temperature of 65° C. for 15 min, by the method of Westphal and Jann (Westphal i Jann, 1965). Collected and pooled water phases were dialysed against distilled water. LPS was separated from nucleic acid via triple ultracentrifugation (105000×g, 6 h.). Purified LPS (200 mg) was subjected to mild acidic hydrolysis with 1.5% acetic acid at 100° C. for 45 min. The solution was centrifuged in order to separate the pellet of lipid A from poly- and oligosaccharides present in water solution (13000 g, 20 min.). The supernatant containing dissolved poly- and oligosaccharides was freeze-dried and subsequently fractionated by gel permeation chromatography, performed on a Bio-Gel P-10, separating O-specific chains from shorter chain polysaccharides and core oligosaccharides. The column was equilibrated with 0.05 M pyridine/acetic acid/water buffer (10/4/986) at pH 5.6. Fractions of volume 1.2 ml (100 drops) were collected, recording continuously refractive index difference between column eluent and control buffer with the use of refractometer (Knauer, Germany). Thus isolated fractions 1, 2, 3, 4, 5, 6, 7 were subjected to the initial structural analysis with the use of MALDI-TOF and/or ESI-MS mass spectrometry in negative ion mode. On the basis of the obtained mass spectra, fractions 1, 2, 3, 4 and 5 were selected as polysaccharide fractions comprising in their structure the O-specific polysaccharide. The MALDI-TOF MS spectrum (negative ion mode, matrix: 2,4,6-trihydroxyacetophenone) recorded for the fraction 5 contained molecular ions of masses corresponding to the polysaccharide PS1 built of structure PD1t-PD1-[Hep]-Kdo (FIG. 1). The major ion at m/z 2452.08 [M-H]$^-$ corresponded to the structure built of two repeating units of the O-specific chain linked to the Hep-Kdo disaccharide and additionally substituted with one O-acetyl group (FIG. 1a), with the first repeating unit devoid of the terminal α-D-Glcp moiety. Calculated monoisotopic mass of the described structure is 2452.79 Da. Ion of mass m/z 2494.08 corresponds to the described structure containing two O-acetyl groups. Additionally for the both aforementioned ions structure versions [M-H$_2$O—H]$^-$ (m/z 2474.05, 2434.09) and [M+Na-H]$^-$ (m/z 2516.06, 2474.07) were observed. Analysis of the MALDI-TOF spectra has shown in the studied fraction the presence of population of molecules devoid of both terminal D-Glcp and one or two O-acetyl groups. Fraction 5 components, sequences of the sugar residues in this polysaccharide and the anomeric configurations of the linkages were established with the use of $^1$H, $^{13}$C- and $^1$H, $^{31}$P-NMR analyses. Series of one- and two-dimensional experiments was performed (COSY, TOCSY, HSQC-DEPT, HMQC, HMBC, NOESY, ROESY). The recorded spectra made it possible to describe of the spin systems of the sugar residues building the polysaccharide of fraction 5 and the results are presented in Table 1. Interpretation of the spectra obtained in the HMBC, NOESY and ROESY experiments according to the rules known to the skilled in the art, allowed for the sequence assignment due to the interresidue connectivities observed through the $^3J_{H,C}$ coupling and NOE for the anomeric protons and carbons. Polysaccharides that are present in fraction 5 are built of two repeating units of the O-specific polysaccharide (FIG. 1) linked to the disaccharide →7)-L-glycero-D-manno-Hep-(1→8)-Kdo. This described link is built of α-(1→7) glycosidic linkage between the first residue GlcNAc (residue C) of the first repeating unit of the O-specific chain and the carbon C-7 of the Kdo (residue A) of the disaccharide (high chemical shift value of the atom C-7, Table 1). The structure of this polysaccharide was presented in the FIG. 1. The presence of the O-acetyl groups in position C-3 of the residues E' and e is the reason for heterogeneity of the polysaccharide observed in the mass spectra. Additionally the first repeating unit is devoid of the terminal α-D-Glcp-(1→(FIG. 1).

Finally, fraction 5 is a mixture of polysaccharides composed of two repeating units of the O-specific polysaccharide of *H. alvei* PCM 1200 LPS that has the following general formula PD1t-(PD1)n-[Hep]-Kdo (where n=1), and for which the structure is shown in FIG. 1a, and the symbol "-[Hep]-Kdo" stands for a structure →7)-[L-glycero-D-manno-Hep-(1→8)-]-Kdo. Analogous analysis was carried out for the fraction 4. Fraction 4 is a mixture of polysaccharides composed of three repeating units of the O-specific polysaccharide of LPS of *H. alvei* PCM 1200 that has the following general formula: PD1$_t$(PD1)$_n$-[Hep]-Kdo (where n=2). Mass spectrum that was recorded for the fraction 4 with the use of MALDI-TOF MS showed a cluster of major [M-H]$^-$ ions, at m/z 3607.8 and m/z 3565.7. Ion at m/z 3607.8 [M-H]$^-$ is attributed to the structure built of three repeating units of the O-specific polysaccharide linked to the Hep-Kdo disaccharide and additionally substituted with one O-acetyl group (FIG. 1a), with one of the repeating units devoid of the terminal α-D-Glcp moiety. Calculated monoisotopic mass of this above described structure is 3608.17 Da. Ion [M-H] at m/z 3565.7 is corresponding to the described structure with one O-acetyl group. In addition for these aforedescribed ions, the ions of type [M+Na-H]$^-$ (m/z 3629.8, 3587.7) and [M-H$_2$O—H]$^-$ (m/z 3591, 3547.7) were also recorded. Analysis of the MALDI-TOF mass spectra indicated also that this studied fraction contained less abundant population of molecules devoid of two terminal α-D-Glcp moieties as well as one or two O-acetyl groups.

We have failed to obtain MALDI-TOF spectra for fractions 3, 2 and 1, containing more than 25 sugar residues. However, according to the results of the analysis of MALDI-TOF MS and NMR for fraction 4 and 5 it can be assumed that these fractions contain polysaccharides built of more than 4 repeating units of the O-specific chain substituting disaccharide Hep-Kdo, having the general formula: PD1-(PD1)$_n$-[Hep]-Kdo (n≥2), where "-[Hep]-KDO" represents a structure →7)-[L-glycero-D-manno-Hep-(1→8)-]-Kdo.

EXAMPLE 6

Preparation of the Reduced Polysaccharide PS1

Polysaccharide fraction PS1 (22 mg) was dissolved in 1 ml of H$_2$O and reduced with NaBH$_4$ (10 mg) for 16 h at 37° C. Solution was acidified with concentrated CH$_3$COOH. The product was purified by gel permeation chromatography performed on a Bio-Gel P-2 column equilibrated with 0.05 M pyridine/acetic acid/water buffer (10:4:986) at pH 5.6. Fractions of volume 1.2 ml were collected recording continuously refractive index difference between mobile phase (column eluent) and control buffer with the use of refractometer (Knauer, Germany). Fraction containing reduced polysaccharide was freeze-dried.

EXAMPLE 7

Preparation of the Conjugate PS1-BSA

The reduced polysaccharide PS1 (22 mg) was dissolved in H$_2$O (2 ml), and the pH of the solution was adjusted to 4.75.

Then 1-ethyl-3-(dimethylaminopropyl)-carbodiimide hydrochloride (50 mg) was added to the continuously stirred solution of the PS1 and pH 4.75 was maintained throughout by addition of 1 M HCl (Lonngren and Goldstein 1978). Reaction was further carried out for 1 h, and subsequently 0.4 ml of water solution of BSA (5 mg/ml) was added. The reaction mixture was incubated for 4 h at room temperature and then neutralized with 1 M $K_2HPO_4$. The product was purified by gel permeation chromatography, performed on a SEPHADEX® G-100 equilibrated with 5% ethanol in water. Fractions of volume 1.2 ml were collected recording continuously refractive index difference between mobile phase (column eluent) and control buffer with the use of refractometer (Knauer, Germany). Obtained and checked for the presence of protein using dot-blotting. Fractions that were containing the conjugate were concentrated using Amicon-ultra 15 to the volume of 1 ml. Half of the product was freeze-dried and half was stored in 0.1% of sodium azide.

EXAMPLE 8

Chemical Immobilization of the Reduced Polysaccharide PS1 on SEPHAROSE 4B® and its Use for Purification of the Ficolin-3 from Human Serum Activation of SEPHAROSE® 4B with bromocyan (BrCN) was carried out according to the method described by Cuatrecasas et al. (Cuatrecasas, 1970). Activated with bromocyanem SEPHAROSE® 4b was bound to diaminoheksane. The gel (SEPHAROSE®-$NH_2$), after washing with water, was suspended in 0.1 M $NaHCO_3$ (pH 9.0). Subsequently, the SEPHAROSE®-$NH_2$ was conjugated with EDC activated $PS_{red}$ 1200. The reaction was carried out for 16 h, at pH 7.5 and temperature of 80° C. Such gel can be used for the purification of the ficolin-3 from human serum and other bodily fluids.

EXAMPLE 9

ELISA Test for the Examination of the Binding of Ficolin-3 (H) to the *H. alvei* 1200 Lipopolysaccharide and PS1200-BSA Conjugate The microtiter MAXISORP® U96 plates (NUNC) were coated with lipopolysaccharide 1200 (FIG. 6A), or the conjugate PS1200-BSA (FIG. 6B). Following the blocking step, assayed solutions of rising concentration of recombinant ficolin-3 (H) were added in high NaCl concentration buffer (Petersen et al., 2001), in order to exclude activation of the complement via the classical pathway (antigen-antibody complex dependent). After incubation for 18 h at 4° C., the binding of the ficolin-3 (H) with LPS was detected with the use of the specific monoclonal antibodies directed against ficolin-3 (H) (clone 4H5, HM2089, HyCult Biotechnology) and horseradish peroxidase-labelled rabbit anti-mouse immunoglobulin antibodies. Recombinant ficolin-3 (H) binds not only native LPS but also the conjugate of PS1200-BSA (the O-specific polysaccharide, the polysaccharide product of hydrolysis of LPS 1200, conjugated with BSA). These two antigens bind both native ficolin-3 (H) from human serum and the recombinant protein. (FIG. 6A, B).

EXAMPLE 10

Binding of the Serum Ficolin-3 (H), Ficolin-2 (L), Ficolin-1 (M), Mannan Binding Lectin (MBL) and the Immunoglobulins to Bovine Serum Albumin, Acetylated Form Thereof and the Lipopolysaccharide *H. alvei* 1200 as Well as to the Polysaccharide Isolated from *H. alvei* 1200 Conjugated with BSA Comparison of binding of the serum ficolin-3 (H), ficolin-2 (L), ficolin-1 (M), mannan binding lectin (MBL) and native immunoglobulins to the acetylated BSA, lipopolysaccharide and the conjugate PS1200-BSA (the polysaccharide isolated from *H. alvei* 1200 conjugated with BSA, PS1-BSA) and unmodified BSA, in two different buffers: recommended by Munthe-Fog ei al. (Munthe-Fog, Hummelshoj et al., 2009) containing Hepes—marked as B1 (25 mM Hepes, 155 mM NaCl, 5 mM CaCl2, 0.1% BSA; pH 7.4) and the hypertonic buffer according to Petersen and co-workers. (Petersen, Thiel et al., 2001) (B2: 20 mM TRIS-HCl, 1M NaCl, 10 mM $CaCl_2$, 0.05% Triton X100, 0.1% BSA; pH 7.4) (FIG. 7). It was demonstrated significantly stronger binding of the ficolin-3 (H) to LPS and PS-BSA *H. alvei* 1200 than to the acetylated albumin, with insignificant binding of the other studied serum elements, that confirms highly specific reaction.

EXAMPLE 11

Comparison of Measurements of the Concentration of Ficolin-3 (H) in Adult Healthy Donors with the Use of ELISA Utilizing the Ligand of PS1200-BSA and the Method of "Sandwich" Type In four serum samples obtained from healthy adult volunteers the concentration of the ficolin-3 (H) was measured by the ELISA, using as a standard the recombinant form of ficolin-3 for which the ligand was the PS1200-BSA (the polysaccharide of *H. alvei* 1200 conjugated with BSA). The following values were measured: 28030 ng/ml; 16926 ng/ml i 9973 ng/ml. With the use of "sandwich" type ELISA described in literature (Munthe-Fog, Hummelshoj et al., 2009), the obtained results were 32700 ng/ml, 19500 ng/ml, and 12000 ng/ml, respectively (we would like to thanks for kind assistance of Prof. Jens C. Jensenius, Aarhus University, Denmark). These results were, in line with expectations, slightly higher due to the measurement of total concentration of ficolin-3 (H), while the proposed method utilizing the conjugate PS1200-BSA allows for the measurement of the biologically active protein only.

EXAMPLE 12

Determination of the Ficolin-3 Concentrations in Sera of Healthy Adult Donors, Based on the ELISA Test Using the Ligand BSA-PS1200

Individual concentration values of ficolin-3 were determined by ELISA in sera obtained from 25 healthy adult donors. The plates (MAXISORP®U96) were coated with PS1200-BSA conjugate (the polysaccharide of *H. alvei* 1200 conjugated with BSA). After the blocking step, the test sera diluted 1:200 in buffer B2 (20 mM Tris-HCl, 1M NaCl, 10 mM$CaCl_2$, 0.05% Triton X100, 0.1% BSA, pH 7.4) were added. Bound protein was detected using monoclonal antibodies against ficolin-3 (H) (clone 4H5) and horseradish peroxidase-labelled anti-mouse immunoglobulin antibodies. Human serum with a predetermined (with respect to the recombinant protein) concentration of ficolin-3 (H) used as the reference. The results of individual determinations of concentrations of ficolin-3 (H) are shown on FIG. 8. The average concentration was 19,251 ng/ml (median: 17,622 ng/ml, range: 8,751-34,675 ng/ml).

EXAMPLE 13

Figure 10:
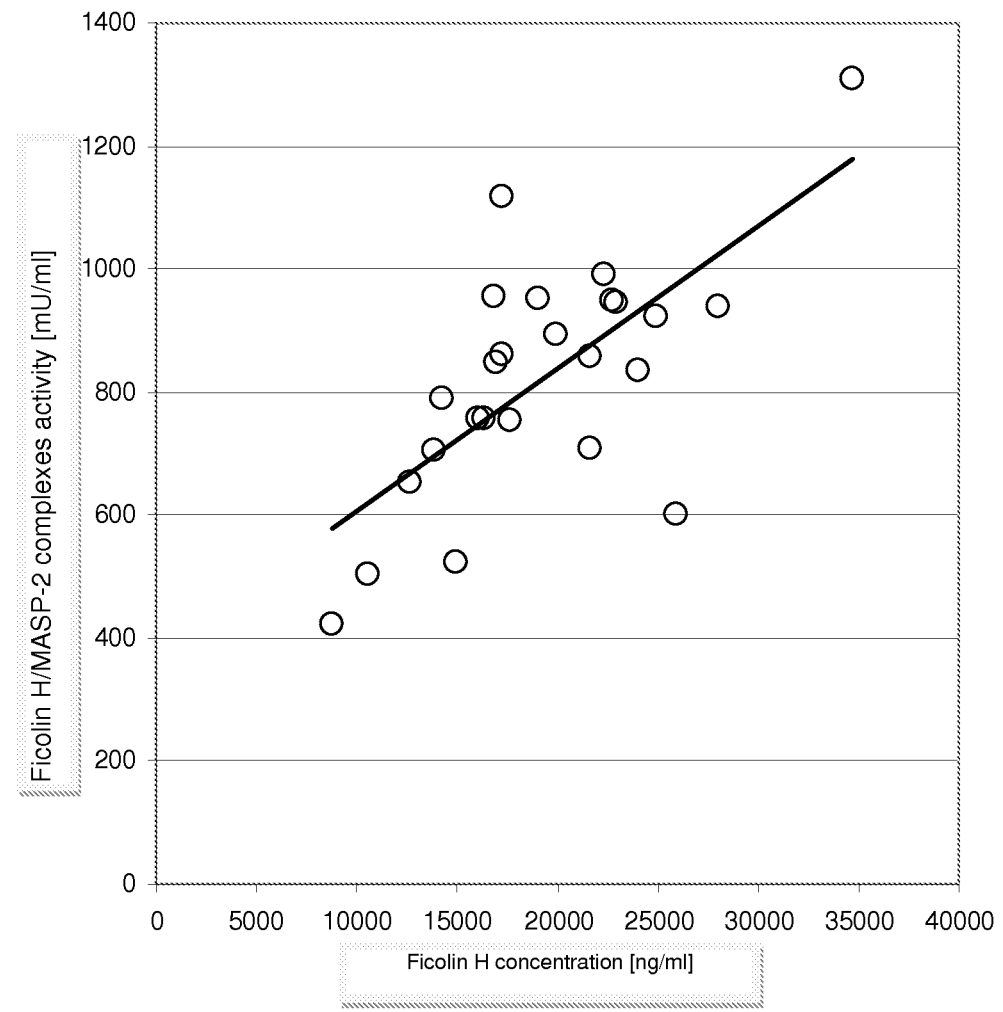

Determination of the Activity of the Complexes Ficolin-3\MASP-2 in Healthy Adult Donors, Based on the ELISA Using PS1200-BSA Ligand MAXISORP® plates U96 were coated with PS-BSA *H. alvei* 1200 and used to determine the ability of complexes of ficolin-3 MASP-2 to activate exogenous C4 component. Serum of a known concentration of ficolin-3 was used again as the reference. It was assumed that the activity of the complexes ficolin-3\MASP-2 of the serum is 1000 mU/ml. Average activity of the complexes ficolin-3\MASP-2 among the 25 sera tested was 822 mU/ml (median: 847 mU/ml, range: 421-1309 mU/ml). The results obtained for the individual measurements of the activity of complexes ficolin-3 \ MASP-2 s are shown on FIG. 9. A statistically significant correlation between the concentration of ficolin-3 and the activity of its complexes with MASP-2 in the test sera was observed in the studied sera (Pearson correlation coefficient R=0.683, p<0.0002) (FIG. 10).

TABLE 1

Chemical shift values for $^1$H and $^{13}$C ($\delta_C$, $\delta_H$) of constituents of fraction 5 isolated from LPS *H. alvei* PCM 1200.

| | Residue | $J_{H1,C1}$ | H1/C1 | H2/C-2 | H3/C3 (H3ax, H3eq) | H4/C4 ($^{TM}_P$) | H5/C5 | H6a, 6b/C6 | H7a, 7b/C7 | H8a, 8b/C8 |
|---|---|---|---|---|---|---|---|---|---|---|
| A | →7,8)-α-Kdop-(2→ | — | —/174 | —/96.7 | (1.80, 2.05)/34.2 | 4.05/65.9 | 4.14/66.2 | 4.03/69.0$^a$ | 4.10/ 75.7$^a$ | 3.51, 3.74/ 64.4 |
| B | L-glycero-α-D-manno-Hepp-(1→$^a$ | 173 Hz | 4.77/99.3 | 3.89/69.9 | 3.82/70.8 | 3.83/66.2 | 3.59/71.4 | 3.98/69.3 | 3.58, 3.66/ 63.7$^a$ | |
| C/[c] | →3)-α-D-GlcpNAc-(1→ | 177 Hz | 5.05/97.3 | 4.03/52.3 | 3.95/79.4 [3.86/82.5] | 3.65/67.7 | 4.20/71.2 | 3.85, 3.78/60.1 | | |
| D | →2,3)-β-D-Galp-(1→ | 168 Hz | 4.58/100.7 | 3.87/75.1 | 4.27/78.6 | 4.10$^b$/67.7 | 3.70$^c$/74.9 | 3.77-3.70$^d$/60.8 | | |
| D' | →2,3)--D-Galp-(1→ | 168 Hz | 4.57/100.8 | 3.91/75.1 | 4.29/78.6 | 4.10$^b$/67.7 | 3.70$^c$/74.9 | 3.77-3.70$^d$/60.9 | | |
| d | →2,3,4)-β-D-Galp-(1→ | 166 Hz | 4.66/100.2 | 3.97/74.6 | 4.36/77.5 | 4.19/76.9 | 3.75$^a$/75.0 | n/60.2 | | |
| E | β-D-GlcpNAc-(1→ | 166 Hz | 4.91/100.4 | 3.76/55.5 | 3.51$^a$/75.0 | 3.45/70.0 | 3.43/76.2 | 3.73, 3.91/60.9 | | |
| E' | β-D-GlcpNAc3OAc-(1→ | 165 Hz | 5.03/99.7 | 3.84/54.0 | 4.93/77.2 | 3.59/68.0 | 3.51/76.1 | 3.72, 3.93/60.9 | | |
| e | β-D-GlcpNAc3OAc-(1→ | 165 Hz | 5.05/99.7 | 3.87/53.9 | 4.98/76.7 | 3.67/67.7 | 3.53/76.1 | 3.76, 3.91/60.9 | | |
| f | α-D-Glcp-(1→ | 173 Hz | 5.00/100.3 | 3.51/72.1 | 3.76/72.4 | 3.48/69.5 | 3.94$^d$/72.2 | 3.84, 3.95$^d$/60.1 | | |
| G | →1)-Gro-(3-P→ | — | 3.70, 3.99/ 70.8$^e$ | 4.07/69.5$^f$ | 4.01, 3.93/ 66.5 | (0.76) | | | | |
| g | →1)-Gro-(3-P→ | — | 3.70, 3.99/ 70.8$^e$ | 4.07/69.5$^f$ | 4.04, 3.98/ 66.5 | (0.19) | | | | |
| H | →3)-β-D-Quip4NAc-(1→ | 164 Hz | 4.45/102.8 | 3.41/72.5 | 3.68/77.4 | 3.71/56.7 | 3.51/71.2 | 1.16/16.5 | | |
| h | β-D-Quip4NAc-(1→ | 164 Hz | 4.44/102.8 | 3.36/73.8 | 3.50/73.5 | 3.57/56.7 | 3.56/71.2 | 1.20/16.9 | | |

$^a$Spectra $^1$H, $^{13}$C NMR were obtained with the use of 600 MHz Bruker Avance II spectrometer at 303 K. Residues marked with upper-case letters refer to the first repeating unit from the reducing end of the O-specific polysaccharide.
Residues marked with lower-case letters refer to the constituents of the second repeating unit.
Internal standard: acetone ($\delta_H$ 2.225, $\delta_C$ 31.05);
n—not determined chemical shift value,
a) Tentative assignment in agreement with the reference (Dag, Niedziela et al., 2004);
$^{b,c,d,e,f}$— not resolved signals.

TABLE 2

Selected inter-residue NOE and $^3$J connectivities between anomeric protons and carbons observed for the fraction 5 isolated from *H. alvei* 1200 LPS.

| | | Atom | Connectivity to | | Interpretation of a |
|---|---|---|---|---|---|
| | Residue | $\delta_H/\delta_C$ (ppm) | $\delta_C$ | $\delta_H$ | signal |
| B | L-glycero-α-D-manno-Hepp-(1→$^a$ | 4.77/99.3 | 64.2 | | C-8 of A |
| | | | 71.4 | | C-5 of B |
| | | | 70.9 | | C-3 of B |
| c | →3)-α-D-GlcpNAc-(1→ | 5.05/97.3 | 77.2 | 3.68* | C-3, H-3 of H |
| D | →2,3)-β-D-Galp-(1→ | 4.58/100.7 | | 3.71 | H-5 of D' |
| | | | 82.3 | 3.86 | C-3, H-3 of c |

TABLE 2-continued

Selected inter-residue NOE and $^3$J connectivities between anomeric protons and carbons observed for the fraction 5 isolated from *H. alvei* 1200 LPS.

| Residue | Atom $\delta_H/\delta_C$ (ppm) | Connectivity to $\delta_C$ | $\delta_H$ | Interpretation of a signal |
|---|---|---|---|---|
| D' →2,3)-β-D-Galp-(1→ | 4.57/100.8 | | 3.71 | H-5 of D |
| | | 82.3 | 3.86 | C-3, H-3 of c |
| d →2,3,4)-β-D-Galp-(1→ | 4.66/100.2 | 79.3 | 3.94* | C-3, H-3 of C |
| | | | 3.74 | H-5 of d |
| E β-D-GlcpNAc-(1→ | 4.91/100.4 | 75.1 | 3.87/3.91 | C-2, H-2 of D/D' |
| E' β-D-GlcpNAc3OAc-(1→ | 5.03/99.7 | 75.2 | 3.87/3.91 | C-2, H-2 of D/D' |
| f α-D-Glcp-(1→ | 5.00/100.3 | 73.0 | | C-3 of f |
| | | | 4.19 | H-4 of d |
| G →1)-Gro-(3-P→[b] | H-3a,b/C-3 4.01, 3.93/66.5 $\delta_P$: 0.76 | | 4.28 | H-3 of D,D' |
| g →1)-Gro-(3-P→[b] | H-3a,b/C-3 4.04, 3.98/66.5 $\delta_P$: 0.19 | | 4.35 | H-3 of d |
| H →3)-β-D-Quip4NAc-(1→ | 4.45/102.8 | 70.9 | 3.69, 4.00 | C-1, H-a,b of G |
| h β-D-Quip4NAc-(1→ | 4.44/102.8 | 70.9 | 3.69, 4.00 | C-1, H-a,b of g |

[a]$^1$H, $^{13}$C NMR spectra were obtained on a Bruker Avance II 600 MHz spectrometer at 303 K. Residues marked with upper-case letters refer to the first repeating unit from the reducing end of the O-specific polysaccharide. Residues marked with lower-case letters refer to the constituents of the second repeating unit.
[a]Values marked with asterisks represent NOE connectivity only.
[b]$^1$H, $^{31}$P-HMQC correlations showing the linkage between phosphate groups and appropriate atom observed for G and g residues.

REFERENCES

Aderem, A. and R. J. Ulevitch (2000). "Toll-like receptors in the induction of the innate immune response." *Nature* 406: 787.

Andersen, T., L. Munthe-Fog, P. Garred and S. Jacobsen (2009). "Serum levels of ficolin-3 (Hakata antigen) in patients with systemic lupus erythematosus." *J Rheumatol* 36(4): 757-9.

Atkinson, A. P., M. Cedzynski, J. Szemraj, A. St Swierzko, L. Bak-Romaniszyn, M. Banasik, K. Zeman, M. Matsushita, M. L. Turner and D. C. Kilpatrick (2004). "L-ficolin in children with recurrent respiratory infections." *Clin Exp Immunol* 138(3): 517-20.

Cedzynski, M., A. P. Atkinson, A. St Swierzko, S. L. Mac-Donald, A. Szala, K. Zeman, K. Buczylko, L. Bak-Romaniszyn, M. Wiszniewska, M. Matsushita, J. Szemraj, M. Banasik, M. L. Turner and D. C. Kilpatrick (2009). "L-ficolin (ficolin-2) insufficiency is associated with combined allergic and infectious respiratory disease in children." *Mol Immunol* 47(2-3): 415-9.

Cedzynski, M., L. Nuytinck, A. P. Atkinson, A. St Swierzko, K. Zeman, J. Szemraj, A. Szala, M. L. Turner and D. C. Kilpatrick (2007). "Extremes of L-ficolin concentration in children with recurrent infections are associated with single nucleotide polymorphisms in the FCN2 gene." *Clin Exp Immunol* 150(1): 99-104.

Cuatrecasas, P. J. (1970). "Protein purification by affinity chromatography. Derivatizations of Agarose and polyacrylamide Beads." *Journal of Biological Chemistry* 245: 3059-3065.

Dag, S., T. Niedziela, M. Dzieciatkowska, J. Lukasiewicz, W. Jachymek, C. Lugowski and L. Kenne (2004). "The O-acetylation patterns in the O-antigens of *Hafnia alvei* strains PCM 1200 and 1203, serologically closely related to PCM 1205." *Carbohydr Res* 339(15): 2521-7.

Degn, S. E., A. G. Hansen, R. Steffensen, C. Jacobsen, J. C. Jensenius and S. Thiel (2009). "MAp44, a human protein associated with pattern recognition molecules of the complement system and regulating the lectin pathway of complement activation." *J Immunol* 183(11): 7371-8.

Fukutomi, T., B. Ando, S. Sakamoto, H. Sakai and H. Nawata (1996). "Thermolabile beta-2 macroglycoprotein (Hakata antigen) in liver disease: biochemical and immunohistochemical study." *Clin Chim Acta* 255(2): 93-106.

Gamian, A., E. Romanowska, U. Dabrowski and J. Dabrowski (1991). "Structure of the O-specific, sialic acid containing polysaccharide chain and its linkage to the core region in lipopolysaccharide from *Hafnia alvei* strain 2 as elucidated by chemical methods, gas-liquid chromatography/mass spectrometry, and $^1$H NMR spectroscopy." *Biochemistry*. 30(20): 5032-8.

Garlatti, V., L. Martin, M. Lacroix, E. Gout, G. J. Arlaud, N. M. Thielens and C. Gaboriaud "Structural Insights into the Recognition Properties of Human Ficolins." *Journal of Innate Immunity* 2(1): 17-23.

Garred, P., C. Honore, Y. J. Ma, S. Rorvig, J. Cowland, N. Borregaard and T. HummelshÅj (2010). "The Genetics of Ficolins." *Journal of Innate Immunity* 2(1): 3-16.

Garred, P., C. Honore, Y. J. Ma, L. Munthe-Fog and T. Hummelshoj (2009). "MBL2, FCN1, FCN2 and FCN3—The genes behind the initiation of the lectin pathway of complement." *Mol Immunol* 46(14): 2737-44.

Gout, E., V. Garlatti, D. F. Smith, M. M. Lacroix, C. Dumestre-Perard, T. Lunardi, L. Martin, J. Y. Cesbron, G. J. Arlaud, C. Gaboriaud and N. M. Thielens (2010). "Carbohydrate recognition properties of human ficolins: Glycan array screening reveals the sialic acid binding specificity of M-ficolin." *J Biol. Chem.* 285(9): 6612-22

Herpers, B. L., B. A. de Jong, B. Dekker, P. C. Aerts, H. van Dijk, G. T. Rijkers and H. van Velzen-Blad (2009). "Hemolytic assay for the measurement of functional human mannose-binding lectin: a modification to avoid interference from classical pathway activation." *J Immunol Methods* 343(1): 61-3.

Hoist, O., A. J. Ulmer, H. Brade, H. Flad and E. Rietschel (1996). "Biochemistry and cell biology of bacterial endotoxins." *FEMS Immunology and Medical Microbiology* 16: 83-104.

Inoshita, H., M. Matsushita, S. Koide, G. Kusaba, M. Ishii, K. Onda, M. J. Gi, M. Nakata, I. Ohsawa, S. Horikoshi, H. Ohi and Y. Tomino (2009). "A novel measurement method for activation of the lectin complement pathway via both mannose-binding lectin (MBL) and L-ficolin." *Journal of Immunological Methods* 349(1-2): 9-17.

Jachymek, W., J. Czaja, T. Niedziela, C. Lugowski and L. Kenne (1999). "Structural studies of the O-specific polysaccharide of *Hafnia alvei* strain PCM 1207 lipopolysaccharide." *European Journal of Biochemistry* 266(1): 53-61.

Jachymek, W., C. Petersson, A. Helander, L. Kenne, C. Lugowski and T. Niedziela (1995). "Structural studies of the O-specific chain and a core hexasaccharide of *Hafnia alvei* strain 1192 lipopolysaccharide." *Carbohydrate Research* 269(1): 125-38.

Katzenellenbogen, E., N. A. Kocharova, G. V. Zatonsky, M. Bogulska, D. Witkowska, A. S. Shashkov, Y. A. Knirel and E. Romanowska (1999). "Structure of the O-specific polysaccharide of *Hafnia alvei* 23 having an oligosaccharide-phosphate repeating unit." *Journal of Carbohydrate Chemistry* 18(5): 545-558.

Katzenellenbogen, E., E. Romanowska, N. A. Kocharova, Y. A. Knirel, A. S. Shashkov and N. K. Kochetkov (1992). "The structure of a glycerol teichoic acid-like O-specific polysaccharide of *Hafnia alvei* 1205." *Carbohydr Res.* 231: 249-60.

Kilpatrick, D. C., T. Fujita and M. Matsushita (1999). "P35, an opsonic lectin of the ficolin family, in human blood from neonates, normal adults, and recurrent miscarriage patients." *Immunol Lett* 67(2): 109-12.

Lacroix, M., C. Dumestre-Perard, G. Schoehn, G. Houen, J. Y. Cesbron, G. J. Arlaud and N. M. Thielens (2009). "Residue Lys57 in the collagen-like region of human L-ficolin and its counterpart Lys47 in H-ficolin play a key role in the interaction with the mannan-binding lectin-associated serine proteases and the collectin receptor calreticulin." *J Immunol* 182(1): 456-65.

Liu, Y., Y. Endo, D. Iwaki, M. Nakata, M. Matsushita, I. Wada, K. Inoue, M. Munakata and T. Fujita (2005). "Human M-ficolin is a secretory protein that activates the lectin complement pathway." *J Immunol* 175(5): 3150-6.

Lonngren, J. and I. J. Goldstein (1978). Carbohydrate antigens: coupling melibionic acid to bovine serum albumin using water-soluble carbodiimide. *Methods in Enzymology* V. Ginsburg. N.Y., San Francisco, London, Academic Press. 50: 160-162.

Lukasiewicz, J., T. Niedziela, W. Jachymek, L. Kenne and C. Lugowski (2009). "Two Kdo-heptose regions identified in *Hafnia alvei*±32 lipopolysaccharide: the complete core structure and serological screening of different *Hafnia* 0 serotypes." *J. Bacteriol.* 191(2): 533-44. Epub 2008 Nov. 14.

Matsushita, M. (2007). The ficolin family: an overwiev. *Collagen-related lectins in innate immunity*. D. Kilpatrick. Kerala, Trivandrum, Research Signpost: 17-32.

Matsushita, M. (2010). "Ficolins: complement-activating lectins involved in innate immunity." *Journal of Innate Immunity* 2(1): 24-32.

Matsushita, M., M. Kuraya, N. Hamasaki, M. Tsujimura, H. Shiraki and T. Fujita (2002). "Activation of the lectin complement pathway by H-ficolin (Hakata antigen)." *J Immunol* 168(7): 3502-6.

Munthe-Fog, L., T. Hummelshoj, C. Honore, H. O. Madsen, H. Permin and P. Garned (2009). "Immunodeficiency associated with FCN3 mutation and ficolin-3 deficiency." *N Engl J Med* 360(25): 2637-44.

Niedziela, T., C. Petersson, A. Helander, W. Jachymek, L. Kenne and C. Lugowski (1996). "Structural studies of the O-specific polysaccharide of *Hafnia alvei* strain 1209 lipopolysaccharide." *European Journal of Biochemistry* 237(3): 635-41.

Petersen, S. V., S. Thiel, L. Jensen, R. Steffensen and J. C. Jensenius (2001). "An assay for the mannan-binding lectin pathway of complement activation." *J Immunol Methods.* 257(1-2): 107-16.

Petersson, C., W. Jachymek, L. Kenne, T. Niedziela and C. Lugowski (1997). "Structural studies of the O-specific chain of *Hafnia alvei* strain PCM 1190 lipopolysaccharide." *Carbohydrate Research* 298(3): 219-27.

Rietschel, E. T., H. Brade, O. Hoist, L. Brade and e. al. (1996). Bacterial endotoxin: chemical constitution, biological recognition, host response, and immunological detoxification. *Pathology of Septic Shock*. E. T. Rietschel and H. Wagner. Berlin, Heidelberg, N.Y., Springer-Verlag: 40-81.

Runza, V. L., W. Schwaeble and D. N. Mannel (2008). "Ficolins: novel pattern recognition molecules of the innate immune response." *Immunobiology* 213(3-4): 297-306.

Schlapbach, L. J., C. Aebi, A. G. Hansen, A. Hirt, J. C. Jensenius and R. A. Ammann (2009). "H-ficolin serum concentration and susceptibility to fever and neutropenia in paediatric cancer patients." *Clin Exp Immunol* 157(1): 83-9.

Sugimoto, R., Y. Yae, M. Akaiwa, S. Kitajima, Y. Shibata, H. Sato, J. Hirata, K. Okochi, K. Izuhara and N. Hamasaki (1998). "Cloning and characterization of the Hakata antigen, a member of the ficolin/opsonin p35 lectin family." *J Biol Chem* 273(33): 20721-7.

Svendsen, C. B., T. Hummelshoj, L. Munthe-Fog, N. Milman, P. Garred, I. A. Laursen, M. Christiansen and K. A. Krogfelt (2008). "Ficolins and Mannose-Binding Lectin in Danish patients with sarcoidosis." *Respir Med* 102(9): 1237-42.

Swierzko, A. S., A. P. Atkinson, M. Cedzynski, S. L. MacDonald, A. Szala, I. Domzalska-Popadiuk, M. Borkowska-Klos, A. Jopek, J. Szczapa, M. Matsushita, J. Szemraj, M. L. Turner and D. C. Kilpatrick (2009). "Two factors of the lectin pathway of complement, L-ficolin and mannan-binding lectin, and their associations with prematurity, low birthweight and infections in a large cohort of Polish neonates." *Mol Immunol* 46(4): 551-8.

Thiel, S. (2007). "Complement activating soluble pattern recognition molecules with collagen-like regions, mannan-binding lectin, ficolins and associated proteins." *Mol Immunol* 44(16): 3875-88.

Tsujimura, M., T. Miyazaki, E. Kojima, Y. Sagara, H. Shiraki, K. Okochi and Y. Maeda (2002). "Serum concentration of Hakata antigen, a member of the ficolins, is linked with inhibition of *Aerococcus viridans* growth." *Clin Chim Acta* 325(1-2): 139-46.

Wang, C. C., K. W. Yim, T. C. Poon, K. W. Choy, C. Y. Chu, W. T. Lui, T. K. Lau, M. S. Rogers and T. N. Leung (2007). "Innate immune response by ficolin binding in apoptotic placenta is associated with the clinical syndrome of preeclampsia." *Clin Chem* 53(1): 42-52.

Westphal, O. and K. Jann (1965). "Bacterial lipopolysaccharides: Extraction with phenol-water and further applications of the procedure." *Methods Carbohydr. Chem.* 5: 83-89.

Wittenborn, T., S. Thiel, L. Jensen, H. J. Nielsen and J. C. Jensenius (2010). "Characteristics and biological variations of M-ficolin, a pattern recognition molecule, in plasma." *J Innate Immun* 2(2): 167-80.

Yae, Y., S. Inaba, H. Sato, K. Okochi, F. Tokunaga and S. Iwanaga (1991). "Isolation and characterization of a thermolabile beta-2 macroglycoprotein ('thermolabile substance' or 'Hakata antigen') detected by precipitating (auto) antibody in sera of patients with systemic lupus erythematosus." *Biochim Biophys Acta* 1078(3): 369-76.

The invention claimed is:

1. A ficolin-3 binding conjugate, comprising (A) a known carrier protein or chromatographic medium linked to (B) a polysaccharide with an affinity for ficolin-3 comprising an oligosaccharide repeating unit of the general formula:

$$PD_r\text{-}(PD)_n\text{-}[Hep]\text{-}Kdo,$$

wherein:

n is an integer from 0 to 100,

PDt stands for:
the repeating oligosaccharide unit PD1$_t$ of the formula:
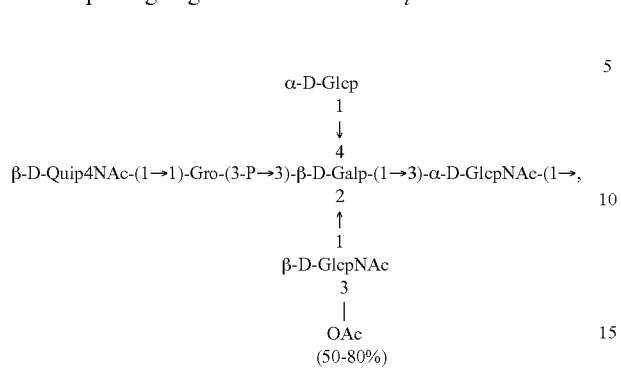
or the repeating oligosaccharide unit PD2$_t$ of the formula:
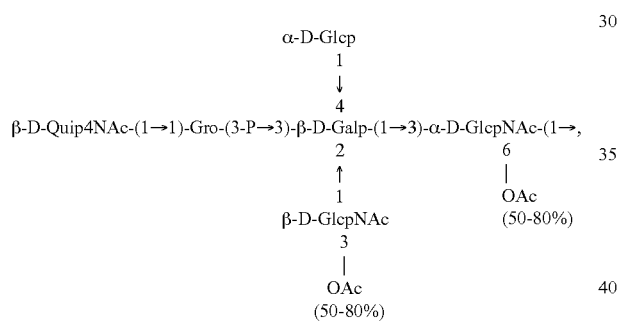
or the repeating oligosaccharide unit PD3$_t$ of the formula:
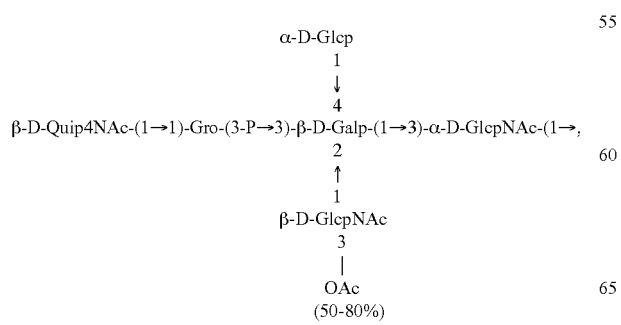
-continued
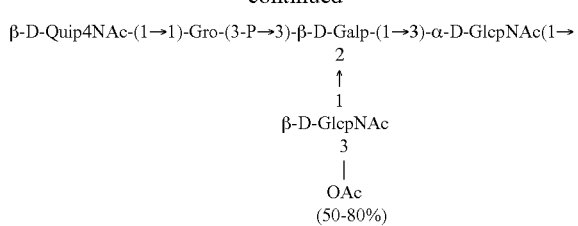
PD stands for:
the repeating oligosaccharide unit PD1 of the formula:
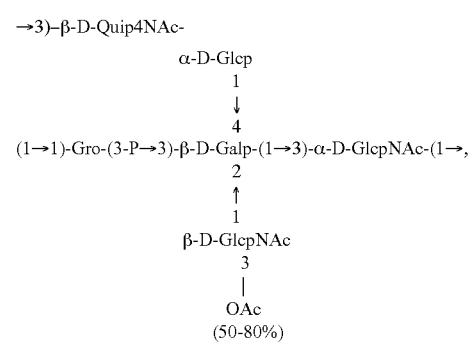
or the repeating oligosaccharide unit PD2 of the formula:
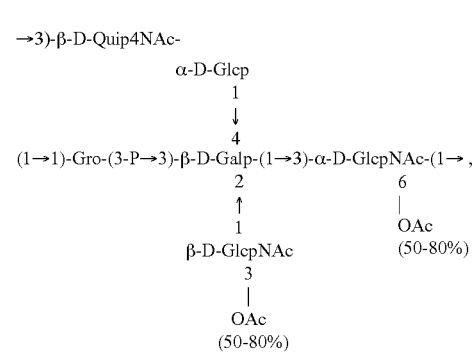

or the repeating oligosaccharide unit PD3 of the formula:

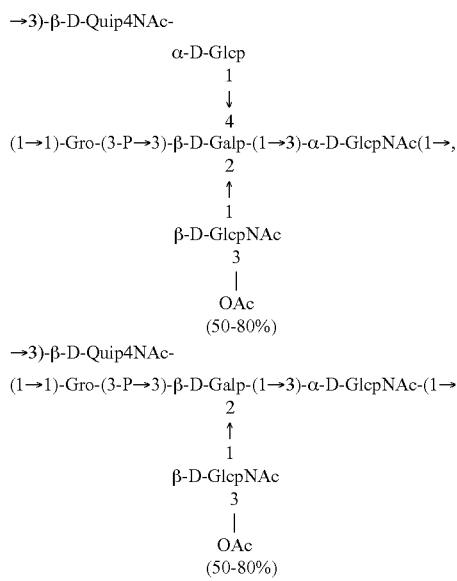

-[Hep]-Kdo stands for the repeating oligosaccharide unit of the formula:

```
    L-α-D-Hepp;
        1
        ↓
        8
    →7)-Kdo
``` wherein the polysaccharide does not comprise a core oligosaccharide of a bacterial lipopolysaccharide (LPS);
wherein the polysaccharide does not comprise a lipid A of a bacterial (LPS); and
wherein the conjugate binds human ficolin-3.

2. The conjugate according to claim 1, wherein the polysaccharide comprises oligosaccharide units selected from units of the general formula:

$$PD1_t\text{-}(PD1)_n\text{-}[Hep]\text{-}Kdo, PD2_t\text{-}(PD2)_n\text{-}[Hep]\text{-}Kdo, \text{ or } PD3_t\text{-}(PD3)_n\text{-}[Hep]\text{-}Kdo.$$

3. The conjugate according to claim 1, wherein the polysaccharide is a reduced polysaccharide of the general formula $PD_t\text{-}(PD)_n\text{-}[Hep]\text{-}Kdo$, wherein the Kdo residue is deoxy-1-carboxy-3-deoxyoctitol.

4. The conjugate of claim 1 wherein n is less than 50.

* * * * *